US005736129A

United States Patent [19]

Medenica et al.

[11] Patent Number: 5,736,129
[45] Date of Patent: Apr. 7, 1998

[54] FLOW CYTOMETRIC PHARMACOSENSITIVITY ASSAY AND METHOD OF CANCER TREATMENT

[76] Inventors: Rajko D. Medenica, One Ocean Point, Port Royal Plantation, Hilton Head Island, S.C. 29928; David K. Powell, 95 Headlands Dr., Hilton Head Island, S.C. 29926

[21] Appl. No.: 559,812

[22] Filed: Nov. 17, 1995

[51] Int. Cl.[6] .......................... A61K 38/19; C12Q 1/06; G01N 33/52

[52] U.S. Cl. .................. 424/85.4; 424/85.1; 424/85.2; 424/85.5; 424/85.6; 435/4; 435/6; 435/29; 435/34; 435/39; 435/40.5; 435/325; 435/347; 436/172

[58] Field of Search ........................... 424/85.1, 85.2, 424/85.4, 85.5, 85.6, 85.7; 435/29, 34, 39, 40.5, 4, 325, 347, 6; 436/813, 800, 172

[56] References Cited

U.S. PATENT DOCUMENTS

| 4,343,782 | 8/1982 | Shapiro | 424/3 |
|---|---|---|---|
| 4,665,020 | 5/1987 | Saunders | 435/7 |
| 5,069,662 | 12/1991 | Bodden | 604/4 |
| 5,229,265 | 7/1993 | Tometsko | 435/6 |

FOREIGN PATENT DOCUMENTS

WO 91/15595  10/1991  WIPO.
WO 95/20148  7/1995  WIPO.

OTHER PUBLICATIONS

Frankfurt et al. Abstract #1715, *Proceedings of the American Association For Cancer Research* (Mar. 1993), vol. 34, p. 288.

Holdaway, Karen M.; Finlay, Graeme J.; and Baguley, Bruce C., Relationship of Cell Cycle Parameters to in vitro and in vivo Chemosensitivity for a Series of Lewis Lung Carcinoma Lines (1992), *Eur. J. Cancer*, vol. 28A, No. 8/9, pp. 1427–1431.

Leone et al., Predictive Value of the Fluorescent Cytoprint Assay (FCA): A Retrospective Correlation Study of In Vitro Chemosensitivity and Individual Responses to Chemotherapy (1991), *Cancer Investigation*, 9(5), pp. 491–503.

Nrgaard et al. (Abstract), Synergistic and antagonistic effects of myeloid growth factors on in vitro cellular killing by cytotoxic drugs, *Leukemia Research* (1993), vol. 17, No. 8, pp. 689–694.

Afanasyev, V.N. et al., *Cytometry.* 14(6):603–9, 1993.

Boike, G.M. et al., *Proc. Annu. Meet. Am. Assoc. Cancer Res.* 30:A1857, 1989.

Bryson, G.J. et al., *Immunology & Cell Biology.* 72(1):35–41, 1994 Feb.

Choy, E.H. et al., *European Journal of Immunology.* 23(10):2676–81, 1993 Oct.

Dao, T. et al., *Cellular Immunology.* 155(2):304–11, 1994 May.

Darzynkiewicz, Z. et al., *Cytometry.* 13(8):795–808, 1992.

Elprana, D. et al., *Anticancer Research.* 12(6B):2229–39, 1992.

Frankfurt, O. et al., *Proc. Annu. Meet. Am. Assoc. Cancer Res.* 33:A3261, 1992.

Frankfurt, O.S., *Proc. Annu. Meet. Am. Assoc. Cancer Res.* 29:A1942, 1988.

Frankfurt, O.S. et al., *Oncology Research.* 5(1):37–42, 1993.

Frankfurt, O. et al., *Proc. Annu. Meet. Am. Assoc. Cancer Res.* 34:A1715, 1993.

Garozzo, A. et al., *Journal of Chemotherapy.* 1(1):59–63, 1989.

Gheuens, E.E. et al., *Cytometry.* 12(7):636–44, 1991.

Gorczyca, W. et al., *Toxicology Letters.* 67(1–3):249–58, 1993 Apr.

Hedley, D.W., Current Perspectives and Future Directions in Clinical Flow Cytometry. Apr. 25–28, 1991, Baltimore, MD, A25.

Huschtscha, L.I. et al., *Experimental Cell Research.* 212 (1):161–5, 1994 May.

Lacombe, F. et al., *Proc. Annu. Meet. Am. Assoc. Cancer Res.* 33:A1201, 1992.

McCloskey, T.W. et al., *Clinical Immunology & Immunopathology.* 71(1):14–8, 1994 Apr.

Nicoletti, I. et al., *Journal of Immunological Methods.* 139(2):271–9, 1991 Jun 3.

(List continued on next page.)

Primary Examiner—Stephen Walsh
Assistant Examiner—Michael D. Pak
Attorney, Agent, or Firm—DeWitt Ross & Stevens SC

[57] ABSTRACT

A method of treating cancer by the use of a multidrug chemotherapeutic regimen determined by in vitro pharmacosensitivity tests. A cell suspension is prepared from a tumor specimen obtained from the patient. The viable tumor cell count within the cell suspension is calculated. The volume of the cell suspension is then adjusted to obtain a base cell concentration by diluting the cell suspension with patient medium in proportion with the viable tumor cell count. A sample of the cell suspension is retained as a negative control sample. Drug samples are then prepared, each drug sample containing a mixture of cell suspension, patient medium, and a drug selected from several drugs, wherein each drug sample contains a different drug which is added to the drug sample in an aliquot amount proportional to the base cell concentration. The drug samples and negative control sample are then incubated. After incubation, the drug samples and negative control sample are stained with a DNA intercalating dye. The cell viability in the drug samples and negative control sample is determined by use of a flow cytometer. The cell viability in the drug samples and negative control sample is compared to determine the pharmacosensitivity of the tumor. A multidrug treatment regimen is then administered to the patient, wherein the regimen includes the drugs shown to be most effective against the tumor in the pharmacosensitivity assay. The treatment has been shown to be especially useful in the simultaneous treatment of primary tumors and their metastases, especially when the chemotherapeutic regimen is administered locoregionally by intra-arterial infusion methods.

14 Claims, No Drawings

OTHER PUBLICATIONS

Pilarski, L.M. et al., *Blood.* 83(3):724–36, 1994 Feb 1.

Riggs, C.E. Jr. et al. *American Society for Clinical Pharmacology & Therapeutics, Ninetieth Annual Meeting.* Mar. 8–10, 1989, Nashville, TN, p. 16.

Shimabukuro, T., *Hinyokika Kiyo–Acta Urologica Japonica.* 34(8):1349–55, 1988. 1988.

Sun, X.M. et al., *Analytical Biochemistry.* 204(2):351–6, 1992 Aug. 1.

Van de Loosdrecht, A.A. et al., *Experimental Hematology.* 21(13):1628–39, 1993 Dec.

Aabo, Kristian et al. "A Dominated and Resistant Subpopulation Causes Regrowth after Response to 1,3–Bis(2–chloroethyl)–1–nitrosourea Treatment of a Heterogeneous Small Cell Lung Cancer Xenograft in Nude Mice," *Cancer Research.* 54:3295–3299 (1994).

Arvelo, F. et al., "Response of a Multidrug–Resistant Human Small–Cell Lung Cancer Xenograft to Chemotherapy," *J. Cancer Res. Clin. Oncol.* 120:17–23 (1993).

Barry, Michael A. et al., "Etoposide–Induced Apoptosis in Human HL–60 Cells is Associated with Intracellular Acidification," *Cancer Research.* 53:2349–2357 (1993).

Bergamaschi, Gaetano et al., "Inhibitors of Tyrosine Phosphorylation Induce Apoptosis in Human Leukemic Cell Lines," *Leukemia.* 7:2012–2018 (1993).

Bradbury, Dawn et al., "Regulation of Bcl–2 Expression and Apoptosis in Acute Myeloblastic Leukaemia Cells by Granulocyte–Macrophage Colony–Stimulating Factor," *Leukemia.* vol. 8. pp. 786–791 (1994).

Bryson, Gregory J. et al., "A Flow Cytometric Study of Cell Death: Failure of Some Models to Correlate with Morphological Assessment," *Immunology and Cell Biology.* 72:35–41 (1994).

Campana, Dario et al., "Stroma–Supported Immunocytometric Assay (SIA): A Novel Method for Testing the Sensitivity of Acute Lymphoblastic Leukemia Cells to Cytotoxic Drugs," *Leukemia.* vol. 7:3 pp. 482–489 (1993).

Catchpoole, Daniel R. et al., "Etoposide–Induced Cytotoxicity in Two Human T–Cell Leukemic Lines: Delayed Loss of Membrane Permeability Rather than DNA Fragmentation as an Indicator of Programmed Cell Death," *Cancer Research.* 53:4287–4296 (1993).

Choy, Ernest H.S. et al., "Chimaeric Anti–CD4 Monoclonal Antibody Cross–Linked by Monocyte Fcy Receptor Mediates Apoptosis of Human CD4 Lymphocytes," *Eur. J. Immunology.* 23:2676–2681 (1993).

Christ, M. et al., "Apoptosis Induced by Oxysterols in Murine Lymphoma Cells and in Normal Thymocytes," *Immunology.* 78:455–460 (1993).

Dao, T. et al., "Natural Human Interferon–α Augments Apoptosis in Activated T Cell Line," *Cellular Immunology.* 155:304–311.

Darzynkiewicz, Z. et al., "Features of Apoptotic Cells Measured by Flow Cytometry," *Cytometry.* 13:795–808 (1992).

Debatin, Klaus–Michael et al., "APO–1–Induced Apoptosis of Leukemia Cells from Patients with Adult T–Cell Leukemia," *Blood.* vol. 81 pp. 2972–2977 (1993).

DeVita, V.T. et al., *Cancer, Principles & Practice of Oncology.* 288–290.

Dole, Mukund et al., "Bcl–2 Inhibits Chemotherapy–Induced Apoptosis in Neuroblastoma," *Cancer Research.* 54:3253–3259 (1994).

Elprana, D. et al., "Chemosensitivity Testing of Xenografted Squamous Cell Carcinomas of the Head and Neck Region," *Anticancer Research.* 12:2229–2240 (1992).

Feldhoff, Pamela W. et al., "Altered Subcellular Distribution of Topoisomerase IIα in a Drug–Resistant Human Small Cell Lung Cancer Cell Line," *Cancer Research.* 54:756–762 (1994).

Fluckiger Anne–Catherine et al, "Interleukin 10 Induces Apoptotic Cell Death of B–Chronic Lymphocytic Leukemia Cells," *J. Exp. Med.* 179: 91–99 (1994).

Gong, Jianping et al., "Different Patterns of Apoptosis of HL–60 Cells Induced by Cycloheximide and Camptothecin," *Journal of Cellular Physiology.* 157:263–270 (1993).

Gorczyca Wojciech et al., "The Cell Cycle Related Differences in Susceptibility of HL–60 Cells to Apoptosis Induced by Various Antitumor Agents," *Cancer Research.* 53:3186–3192 (1993).

Gruber, Astrid et al., "Effect of Verapamil on Daunorubicin Accumulation in Human Leukemic Cells with Different Levels of MDRI Gene Expression," *Leukemia Research.* vol. 17 pp. 353–358 (1993).

Hamburger Anne W. et al., "Primary Bioassay of Human Tumor Stem Cells," *Science.* vol. 197, pp. 461–463.

Huschtscha, L. I. et al., "Identification of Apoptotic and Necrotic Human Leukemic Cells by Flow Cytometry," *Experimental Cell Research.* 212:161–165 (1994).

Hwang, Wei–Shou et al., "Prediction of Chemotherapy Response in Human Leukemia Using In Vitro Chemosensitivity Test," *Leukemia Research.* vol. 17:8 pp. 685–688 (1993).

Isobe, Hiroshi et al., "Doxorubicin Retention and Chemoresistance in Human Mesothelioma Cell Lines," *Int. J. Cancer.* 57:581–585 (1994).

Johnson, P.W.M. et al., "Isolated Follicular Lymphoma Cells are Resistant to Apoptosis and can be Grown In Vitro in the CD40/Stromal Cell System," *Blood.* vol. 82 pp.1848–1857 (1993).

Lacombe, Francis et al., "Detection of Cytarabine Resistance in Patients With Acute Myelogenous Leukemia Using Flow Cytometry," *Blood.* vol. 84 pp.716–723 (1994).

McCloskey, Thomas W. et al., "Use of a Flow Cytometric Assay to Quantitate Apoptosis in Human Lymphocytes," *Clinical Immunology and Immunopathology.* vol. 71 pp. 14–18 (1994).

Miyashita, T. et al., "Bcl–2 Oncoprotein Blocks Chemotherapy–Induced Apoptosis in a Human Leukemia Cell Line," *Blood.* vol. 81 pp. 151–157 (1993).

Nicoletti, I. et al., "A Rapid and Simple Method for Measuring Thymocyte Apoptosis by Propidium Iodide Staining and Flow Cytometry," *Journal of Immunological Methods.* 139:271–279 (1991).

Pantazis, Panayotis et al., "Regression of Human Breast Carcinoma Tumors in Immunodeficient Mice Treated with 9–Nitrocamptothecin: Differential Response of Nontumorigenic and Tumorigenic Human Breast Cells In Vitro," *Cancer Research.* 53:1577–1582 (1993).

Peters, G. J. et al., "Transformation of Mouse Fibroblasts with the Oncogenes H–ras or trk is Associated with Pronounced Changes in Drug Sensitivity and Metabolism," *Int. J. Cancer.* 54:450–455 (1993).

Raghu, Ganapathirama et al., "P–Glycoprotein and Alterations in the Glutathione/Glutathione–Peroxidase Cycle Underlie Doxorubicin Resistance in HL–60–R, a Subclone of the HL–60 Human Leukemia Cell Line," *Int. J. Cancer.* 53:804–911 (1993).

Schadendorf, Dirk et al., "Chemosensitivity Testing of Human Malignant Melanoma," *Cancer.* vol. 73:1 pp. 103–108 (1994).

Smit, E.F. et al., "In Vitro Response of Human Small–Cell Lung–Cancer Cell Lines to Chemotherapeutic Drugs; No Correlation With Clinical Data," *Int. J. Cancer.* 51:71–78 (1992).

Sparrow, Rosemary L. et al., "Common Expression of the Multidrug Resistance Marker P–Glycoprotein in B–Cell Chronic Lymphocytic Leukaemia and Correlation With In Vitro Drug Resistance," *Leukemia Research.* 17:941–947 (1993).

Sun, Xiao–Ming et al., "A Flow–Cytometric Method for the Separation and Quantitation of Normal and Apoptotic Thymocytes," *Analytical Biochemistry.* 204:351–356 (1992).

Takeda, Yuji et al., "Rapid Acceleration of Neutrophil Apoptosis Tumor Necrosis Factor–α," *International Immunology.* vol. 5 pp 691–694 (1993).

te Boekhorst, Peter A.W. et al., "Predominance of Functional Multidrug Resistance (MDR–1) Phenotype in CD34+ Acute Myeloid Leukemia Cells," *Blood.* vol. 82 pp. 3157–3162 (1993).

Toth, C.A. et al., "Type I Interferon Resistance in a Colorectal Cancer Cell Line is Associated With a More Aggressive Phenotype In Vivo," *Br. J. Cancer.* 65:365–368 (1992).

Uckun, Faith M. et al., "Autologous Bone Marrow Transplantation in High–Risk Remission B–Lineage Acute Lymphoblastic Leukemia Using a Cocktail of Three Monoclonal Antibodies Plus Complement and 4–Hydroperoxycyclophosphamide for Ex Vivo Bone Marrow Purging," *Blood.* vol. 79 pp. 1094–1104 (1992).

Van de Loosdrecht, A.A. et al., "Apoptosis in Tumor Necrosis Factor–α–Dependent, Monocyte–Mediated Leukemic Cell Death: A Functional, Morphologic, and Flow–Cytometric Analysis," *Experimental Hematology.* 21:1628–1639 (1993).

Vikhanskaya, Faina et al., "Introduction of Wild–Type p53 in a Human Ovarian Cancer Cell Line not Expressing Endogenous p53," *Nucleic Acids Research.* vol. 22 pp. 1012–1017 (1994).

Yamada, Toshiko et al., "The Human T–Cell Leukemia Virus Type I Tax Protein Induces Apoptosis Which is Blocked by the Bcl–2 Protein," *Journal of Virology.* pp. 3374–3379 (1994).

Zalcberg, John R. et al., "Cellular and Karyotypic Characterization of Two Doxorubicin Resistant Cell Lines Isolated From the Same Parental Human Leukemia Cell Line," *Int. J. Cancer.* 57:522–528 (1994).

Zhu, Y.M. et al., "Wild–Type p53 is Required for Apoptosis Induced by Growth Factor Deprivation in Factor–Dependent Leukaemic Cells," *Br. J. Cancer.* 69:468–472 (1994).

FLOW CYTOMETRIC PHARMACOSENSITIVITY ASSAY AND METHOD OF CANCER TREATMENT

FIELD OF THE INVENTION

The present invention relates generally to a method of in vivo treatment of cancer patients based on in vitro pharmacosensitivity testing, and more specifically to a method of cancer treatment with a chemotherapeutic regimen dictated by flow cytometric pharmacosensitivity tests.

DESCRIPTION OF THE PRIOR ART

PHARMACOSENSITIVITY ASSAYS

Cancer researchers have long been interested in discovering ways to predict the response of different individuals' tumors to different chemotherapeutic agents. However, tumors generally include cancer cells from numerous different tumor cell lines which live together in equilibrium. Different cell lines may be more resistant to chemotherapy than others. Thus, because certain individuals may have tumors with drug-resistant cell lines intermingled with "generic" tumor cell lines, medical personnel cannot simply assume that administration of a drug which is ordinarily effective against a certain type of tumor in most individuals will be effective in a particular individual suffering from that type of tumor. It has long been recognized that because of the heterogeneous nature of tumors and the likelihood of adaptive mutation due to the inherent instability of the tumor genome, a blanket or "off-the-shelf" phamaceutical agent for curing cancer, even a particular type of cancer, is unlikely. Several studies have expressly noted that blanket treatment of a group of patients with a specific anti-cancer drug or drugs often works very well for a subpopulation of the patients, but then either works minimally or not at all for the remainder of the patients because these patients suffer from drug-resistant tumors. Lacombe et al. (1994); Smit et al. (1992). As an example, doxorubicin is commonly administered for lung carcinoma due to its high effectiveness in certain cases, but for certain patients, treatment is virtually ineffective. In short, generic treatment methods frequently do not work with specific individuals because of varying tumor phenotypes.

In response to this problem, some researchers have proposed the use of in vitro pharmacosensitivity assays to substitute for the lack of in vivo dam for individual cancer cases: by testing an individual's tumor response to a chemotherapeutic agent in vitro, the individual's tumor response to that agent in vivo can supposedly be predicted. Most pharmacosensitivity assays currently in use are at least partially based on the pioneering soft agar tumor culture assay of Salmon et al. (1977). Other exemplary pharmacosensitivity assays are the MTT (3-(4,5-dimethyl-thiazol-2-yl)-2,5-diphenyl tetrazolium bromide) test and the dye exclusion assay test. Mossmann (1983); Smit et al., supra (1992); Hwang et al. (1993). The prior art contains several in vitro studies of tumor response according to these assays and correlates in vitro and in vivo results, e.g., Schadendorf et al. (1993).

Unfortunately, the prior art pharmacosensitivity assays suffer from several drawbacks which have prevented their widespread use.

First, as noted by the prior art, some assays are difficult, expensive, and time-consuming to perform. The last of these disadvantages is possibly the greatest hurdle to widespread use of pharmacosensitivity assays since medical personnel frequently cannot afford to expend extended amounts of time performing a pharmacosensitivity assay because of the threat of disease progression. Owing to this disadvantage, the remainder of this disclosure (and the invention disclosed herein) are addressed to a "short-term" assay, that is, a pharmacosensitivity assay that takes less than approximately one week to complete between the time of detection of the disease and the completion of the assay.

Second, as noted by many of the aforementioned studies, many of the prior art pharmacosensitivity assays are not applicable to all types of tumors, e.g., liquid tumors or very hard tumors. As a result, a specific prior art assay cannot be used for all patients, and different patients require different tests tailored to their specific types of tumors. This results in an increase in the overall cost of testing for all patients, and tends to have the effect of reserving assay-based treatment for the wealthy few who can afford such individualized care.

Third, the prior art pharmacosensitivity assays simply do not present an accurate reflection of in vivo drug application. Many of the assays suffer from low correlation between in vitro and in vivo results for particular (or all) tumor types and cell lines.

Due to the disadvantages listed above, the use of short-term pharmacosensitivity assays has been discouraged for use in cancer patient treatment, especially for the primary treatment of newly diagnosed patients; patients for whom it is believed that effective treatment exists; and for patients with a drug-sensitive tumor who fail the first trial of chemotherapy. See, e.g., DeVita et al. (1989). It is believed in the art that short-term phamacosensitivity assays may provide a benefit insofar as they can deter patient exposure to the toxicity of drugs that are unlikely to be effective, but otherwise the assays cannot recommend a patient treatment regimen superior to one devised by an experienced medical practitioner who exercises sound judgment.

USE OF A MULTIDRUG CHEMOTHERAPEUTIC REGIMEN IN CANCER TREATMENT

It is known that a chemotherapeutic treatment regimen utilizing several drugs may be more effective than the best single drug. As summarized by Arvelo et al. (1993), this is due to several reasons. First, separate chemotherapeutic agents have different limiting toxicities and can therefore be combined in doses close to their maximum single-agent level. Second, one agent can fail to reach a disease confined to an organ, as if the tumor were in a pharmacological sanctuary, but other agents may be able to access the organ more efficiently. Third, a degree of potentiation exists between the agents in their efficacy against tumor cells to a greater extent than normal cells. Finally, different cellular mechanisms of resistance can be activated by different agents.

Those who treat cancer are still left with the problem of choosing the chemotherapeutic drugs to be used in a multidrug treatment regimen. There are literally hundreds of potential chemotherapeutic agents to combine with a wide variety of possible individual dosages, resulting in an infinite number of possible multidrug regimens. Medical personnel are generally inclined to apply one or more drugs shown by the prior art to be effective alone or in combination against the particular type of tumor to be treated. However, as noted above, there is no guarantee that "off-the-shelf" treatments will be effective against particular individuals' tumor cell lines. The use of a pharmacosensitivity assay could help medical personnel to choose the most effective drugs for use in a multidrug treatment regimen, but the prior art pharmacosensitivity assays, which generally require considerable time and expense to screen the effectiveness of a single drug or a handful of drugs, are too inefficient to allow the screening of dozens of drugs. In view of the above considerations, those who suffer from cancer are in need of a method of cancer treatment which allows fast and easy determination and administration of an effective multidrug chemotherapeutic regimen which is particularly tailored to the needs of the individual, i.e., a method of cancer treatment which accounts for all of the unique specific cell lines within the individual's tumor.

APOPTOSIS

There are two major morphologically and biochemically distinct modes of death in nucleated eukaryotic cells: necrosis and apoptosis. Necrosis is essentially degenerative in nature and generally arises due to severe injury to cells. Apoptosis, on the other hand, is associated with the process of physiological cell death and appears to play a role opposite that of mitosis. Apoptosis is a mechanism by which a variety of cell types are deleted during embryonic development (morphogenesis) and hormone-induced organic involution. It also occurs in a variety of normal adult tissues, in particular those with a high cell turnover and during normal aging. Van de Loosdrecht et al. (1993).

Since the efficacy of several chemotherapeutic drugs correlates with their ability to induce apoptosis in tumor cells, the study of apoptosis is of interest to cancer research. Darzynkiewicz et al. (1992). Several researchers have studied the apoptosis-inducing effects of various chemotherapeutic drugs. For example, Christ et al. (1993) studied the effect of oxysterols on apoptosis of RDM4 murine lymphoma and mouse thymocytes in vitro and paralleled the findings of the study with in vivo application. Elprana et al. (1992) performed a similar study on the effects of cisplatin and bleomycin on squamous cell carcinomas obtained from the head and neck region. Lacombe et al., supra (1994) compared the results of in vitro application of Ara-C to acute myeloid leukemia with in vivo results and found good correlation. Campana et al. (1993) tested the in vitro sensitivity of lymphoblasts from acute lymphoblastic leukemia in response to five anti-leukemic drugs and compared the results to in vivo response.

Other researchers have similarly investigated the effects of certain biological response modifiers, e.g., interferons, on apoptosis. Dao et al. (1994); Thoth et al. (1992); Fluckiger et al. (1994).

During research, apoptotic cells may be detected in several ways. First, apoptotic cells illustrate internucleasomal cleavage of nuclear DNA into nucleosome-sized fragments of 200 base pair oligonucleosomal subunits. This registers as a ladder-like pattern on agarose gel slabs following electrophoretic separation. Additionally, Nicoletti et al. (1991) describes a method for detecting apoptotic cells by flow-cytometric analysis of isolated nuclei stained with propidium iodide (PI), an intercalating DNA stain, in hypotonic buffer. The highly-charged PI molecules cannot penetrate the membranes of living cells but are able to penetrate the intact membranes of dead, i.e., apoptotic, cells. When excited by laser light from a flow cytometer at 488 nm, the PI emits red fluorescence at 540 nm, allowing the flow cytometer to easily detect and count the apoptotic cells. The prior art discloses modification of the Nicoletti et al., supra (1991) method wherein other DNA stains are used as well, for example, acridine orange, Hoechst 33342, and ethidium bromide. Darzynkiewicz et al., supra (1992); Bryson, (1994); Huschtscha et al. (1994); Sun et al. (1992).

SUMMARY OF THE INVENTION

The present invention is directed to a method for treating cancer comprising the following steps. A cancer cell suspension is prepared from a specimen taken from a human cancer patient's tumor. The cell suspension is purified of non-cancer cell components, e.g., blood cells, by separating these components out by use of monoclonal antibodies and magnetic beads, or other separation means. Several drug samples, hereinafter referred to as "drug samples," are then prepared from the cell suspension and several putative cancer cell growth-inhibiting drugs, i.e., drugs which are believed to be likely candidates for chemotherapeutic treatment of the tumor. Each drug sample contains a mixture of at least one drug and the cell suspension. The drug samples are then incubated. After incubation, the tumor cell viability of each drug sample is determined to obtain a measure of the tumor cell pharmacosensitivity (the tumor cell response) to the drugs. A drug treatment regimen is then selected for the patient on the basis of the measured tumor cell viabilities for the drug samples. The drugs used in the treatment regimen are chosen from the drugs corresponding to the drug samples having the lowest tumor cell viability. The drug treatment regimen is administered to the patient in an amount which is effective to inhibit the growth of the cancer.

The present invention is additionally directed to a method for treating cancer comprising the following steps. A cell suspension is prepared from a cancer specimen obtained from a human cancer patient. A sample of the cell suspension is retained as a control sample. Drug samples are then prepared from the cell suspension and several putative cancer cell growth-inhibiting drugs, that is, drugs which are of interest as potential candidates for a multidrug chemotherapeutic regimen. Each drug sample contains a mixture of the cell suspension and at least one drug. The control sample and drug samples are then incubated. After incubation, the control samples and drug samples are stained with a DNA intercalating dye, and the cancer cell viability in the control sample and the drug samples is determined by use of a flow cytometer. The cancer cell viability of each drug sample is compared to the cancer cell viability of the control sample to determine the efficacy of each drug against the cancer cells. A drug treatment regimen is then prepared for the patient containing selected drugs chosen from the several drugs used in the drug samples. The selected drugs correspond to the drug samples having the lowest cancer cell viability in comparison to the control sample. The drug treatment regimen is administered to the patient in an amount which is effective to inhibit the growth of the cancer.

The present invention is further directed to a method of treating cancer in human cancer patients comprising the following steps. First, a cell suspension is prepared from a cancer specimen taken from a human cancer patient. The viable cancer cell count within the cell suspension is calculated. The volume of the cell suspension is then adjusted to obtain a base cell concentration by diluting the cell suspension with patient medium in proportion with the viable cancer cell count. A sample of the cell suspension is retained as a negative control sample. Drug samples are then prepared, each drug sample containing a mixture of cell suspension, patient medium, and a drug selected from several putative cancer cell growth-inhibiting drugs. Each drug sample contains a different drug which is added to the drug sample in an aliquot amount proportional to the base cell concentration. The drug samples and negative control sample are then incubated. After incubation, the drug samples and negative control sample are stained with a DNA intercalating dye. The cancer cell viability in the drug samples and negative control sample is determined by use of a flow cytometer. The cancer cell viability in the drug samples and negative control sample is compared to determine the pharmacosensitivity of the cancer cells. A drug treatment regimen is formulated by selecting one or more drugs from the several cancer cell growth-inhibiting drugs. The selected drugs correspond to the drug samples having the highest cancer cell pharmacosensitivity. The drug treatment regimen is then administered to the patient in an amount which is effective to inhibit the growth of the cancer.

The invention provides an exceptionally rapid and versatile method of determining and administering an effective multidrug chemotherapeutic treatment regimen to a patient suffering from cancer. It allows the choice of an individualized and optimized chemotherapeutic regimen for a cancer patient in the space of approximately 48–96 hours after surgery or after a biopsy specimen of the tumor is obtained, thereby minimizing the opportunity for disease progression as the procedure is being carried out. Because the choice of the drugs used for the regimen is dictated by the patient's own tumor, the treatment is individualized. Such treatment is preferred over an "off-the-shelf" multidrug treatment because (1) it accounts for all tumor cell lines, and (2) it accounts for drug-resistant tumor cell lines, including the drugs effective against such cell lines and excluding those that are ineffective. It is believed that every different tumor from every different patient has a unique biological behavior, and that the patient will not receive the best possible treatment unless this is recognized. The benefits of the procedure are demonstrated by the fact that 78% of the patients treated by use of the procedure have achieved total or partial remission. Additionally, the mutidrug regimen dictated by the procedure has low toxicity insofar as ineffective chemotherapeutic agents are eliminated from the regimen.

It has been found that the procedure is also highly effective in treating metastases from primary tumors. Quite often, chemotherapeutic treatment is directed primarily toward the primary tumor and only secondarily to metastases. As a result, even where the primary tumor is defeated, the patient proceeds to perish from the metastatic tumors. This is because treatment tailored for a particular (and often organotropic) primary tumor may be ill-suited for the treatment of distant metastases elsewhere. By developing a treatment regimen on the basis of the sensitivity of the particular cell lines rather than the type or location of a primary tumor, the procedure allows the development of an effective treatment regimen for both primary and metastatic tumors.

The procedure is well-suited for everyday performance in a laboratory. Because the procedure may be used for all types of tumors, and because it may be run for numerous different patients continuously or simultaneously, it is cost-effective for use with practically all cancer patients. The cost of the procedure can be further reduced if one or more of the steps of the procedure are automated.

Apart from the treatment of cancer, the procedure is expected to have application in the treatment of adjuvant therapy, wherein treatment is applied to an individual without evidence of disease due to a high likelihood of the presence of microscopic metastases. As an example, the procedure is expected to have value in the treatment of those who suffer from the Human Immunodeficiency Virus (HIV) where cancer is believed to be present.

The procedure is also useful for assessing the general efficacy of proposed new medications. Presently, proposed chemotherapeutic agents are tested in a broad range of concentrations against approximately 60 different tumor cell lines in a panel performed at the National Cancer Institute. The U.S. Food and Drug Administration (FDA) then uses small animals and rodents to test toxicity. The overall testing process takes a very long time, and as a result, the time lapse between discovery and actual use of a new medication takes an extremely long time. The procedure may be used to rapidly test proposed new chemotherapeutic agents against bone marrow cells to determine the toxicity of the agent, and against different cell lines to determine its efficacy. Because the basic procedure only takes an average of 72 hours to perform, the drug testing process can be greatly accelerated.

Further advantages, features, and objects of the invention will be apparent from the following detailed description of the invention.

DETAILED DESCRIPTION OF THE INVENTION

DEFINITIONS

The following definitions are intended to assist in providing a clear and consistent understanding of the scope and detail of certain terms used throughout this specification.

Biological Response Modifiers: Substances whose origin lies in the human (or animal) body, or which are man-made and mimic particular biological functions of such substances. Biological response modifiers have synergistic effect and produce increased tumor cell kill with a number of chemotherapeutic agents with little, if any, added side effects; have antitumor activity of their own; enhance populations of immune effector cells, such as natural killer cells and cytotoxic T cells; and lower levels of tumor growth factors such as insulin-like growth factor I. Perhaps the best-known biological response modifiers are interferons, a family of over 50 closely related glycoproteins with antiviral, immunoregulatory and antiproliferative functions. The immunoregulatory functions of interferons, such as the enhancement of natural killer lymphocyte activity, the increase in histocompatibility antigens, the activation of monocytes/macrophages, and B cell functions have proven to be of clinical importance, for example, in protecting bone marrow from the toxicity of chemotherapy. As an example, interferon alpha (IFNα) has been found to result in a considerable percentage of clinical remission alone or in combination with other drugs in diseases such as hairy-cell leukemia, chronic myelogenic leukemia, non-Hodgkin's lymphoma, multiple myeloma, and essential thrombocytosis.

The invention includes, but is not limited to, the following biological response modifiers, supplied by the following exemplary manufacturers:

G-CSF, granulocyte-colony stimulating factor or filgrastim, by Amgen, Inc. (Thousand Oaks, Calif. 91320) under the trademark "NEUPOGEN";

GM-CSF, granulocyte macrophage-colony stimulating factor or sargramostim, such as the recombinant human GM-CSF produced by Immunex Corp. (Seattle, Wash. 98101) under the trademark "LEUKINE";

nHuIFNα (natural human leukocyte interferon alpha), by Virogen A. G. (Basel, Switzerland);

nHuIFNαn-3 (natural human leukocyte interferon alpha n-3), by Purdue Frederick Co. under the trademark "ALFERON" (Norwalk, Conn. 06856);

nHuIFNβ (natural human interferon beta or natural human fibroblastic interferon), by Virogen Labs., Basel, Switzerland;

rIFNα-2a (recombinant interferon alpha-2a), by Roche Laboratories, a division of Hoffman-LaRoche Inc. (Nutley, N.J. 07110) under the trademark "ROFERON-A";

rIFNα-2b (recombinant interferon alpha-2b), by Schering Corp. (Kenilworth, N.J. 07033) under the trademark "INTRON-B";

rIFNβ-1b (recombinant interferon beta-1b or fiblaferon), by Berlex Labs. (Richmond, Calif. 94804) under the trademark "BETASERON";

rIFNτ-1b (recombinant interferon gamma-1b or polyferon), by Genentech, Inc. (San Francisco, Calif. 94080) under the trademark "ACTIMMUNE";

rIL-2 (interleukin 2 or aldesleukin) by Chiron Therapeutics (Emeryville, Calif. 94608); and somatostatin, or analogues such as octreotide acetate, by Sandoz Pharmaceuticals, Inc. (East Hanover, N.J. 07936) under the trademark "SANDOSTATIN."

The invention further includes the following biological response modifiers which have been under clinical investigation:

nHuIFNπ-(natural human interferon pi, or antitumor specific interferon), the subject of copending U.S. patent application 07/179,529;

rTNF (recombinant tumor necrosis factor), by Chiron Therapeutics (Emeryville, Calif. 94608).

rIL-3 (interleukin 3), by Sandoz Pharmaceuticals, Inc. (East Hanover, N.J. 07936).

Drug: Throughout this specification, the term "drug" is understood to mean any substance used in the diagnosis, treatment, cure, and prevention of cancer. More specifically, the term "drug" will be used to apply to substances which are known or suspected to directly or indirectly prevent or inhibit the growth of cancer cells, either by directly attacking the cancer cells, by stimulating the body's immune system, or by other means. It is understood that "drug" also encompasses substances which are not believed to prevent or inhibit the growth of cancer cells by themselves, but which are known or suspected to do so when used in combination with one or more other drugs (e.g., mesna, discussed below). The term includes, but is not limited to, chemotherapeutic drugs recognized by the prior art, as well as the biological response modifiers listed above, alkylating agents, antibiotics, antimetabolites, and palliatives or drugs used to combat the side effects of chemotherapy (e . g., antiemetics, antidiarrhetics, hematological growth factors, etc.). As examples, a list of some of the drugs which can be used in the invention follows:

Amethopterin (e.g., "METHOTREXATE" by Lederle Labs.): an antifolate and one of the major antimetabolites used in cancer therapy. Amethopterin is commonly used for treating carcinoma of the breast, head, neck, lung, cervix, penis, prostate, testis, and bladder; acute lymphocytic leukemia; meningeal leukemia; non-Hodgkin's lymphoma; mycosis fungoides; osteosarcoma; and trophoblastic tumors.

Ara-C (Cytosine Arabinoside or Cytarabine, e.g., "CYTOSAR" by Upjohn Co., Kalamazoo, Mich. 49001): an antimetabolite commonly used to promote remission of acute non-lymphocytic (myelocytic) leukemia in adults and children. It has also been found useful in the treatment of acute lymphocytic leukemia, the blast phase of chronic myelocytic leukemia, and non-Hodgkin's lymphoma, but is inactive in most solid tumors.

BCNU (bis(chloroethyl)-nitrosurea or Carmustine, e.g., "BI CNU" by Bristol-Myers Oncology, a Bristol-Myers company, Evansville, Ind. 47721): an alkylating agent commonly used in palliative therapy as a single agent or in combination therapy with other chemotherapeutic drugs. It is also used for treating brain tumors, multiple myelomas, Hodgkin's Disease, and Non-Hodgkin's lymphomas.

Bleomycin (e.g., "BLENOXANE" by Bristol-Myers Oncology, a Bristol-Myers company, Evansville, Ind. 47721): an antitumor antibiotic commonly used in palliative treatment. It has been shown to be useful in the management of squamous cell carcinoma as well as testicular carcinomas and lymphomas.

Cis-platin (cis-platinum, e.g., "PLATINOL" by Bristol-Myers Oncology, a Bristol-Myers company, Evansville, Ind. 47721): a coordination complex of platinum (cisdiaminedichloroplatinum II) commonly used as a palliative treatment for testicular tumors, ovarian tumors and advanced bladder cancer. It has also been shown to promote regression in head and neck cancer as well as lung, cervical, and gastric cancers.

Cladribine (e.g., "LEUSTATIN" by Onho-Biotech, Raritan, N.J. 08869): a cytotoxic drug commonly used for treating hairy cell leukemia.

Cyclophosphamide (e.g., "CYTOXAN" by Bristol-Myers Oncology, a Bristol-Myers company, Evansville, Ind. 47721): an alkylating agent commonly used for treating malignant lymphomas, multiple myeloma, leukemias, neuroblastomas, adenocarcinomas of the ovary, retinoblastomas and breast carcinomas. Although effective alone in susceptible malignancies, it is more frequently used concurrently or sequentially with other antiplastic drugs.

Dactinomycin (Actinomycin-D, e.g., "COSMEGEN" by Merck Sharp & Dohme, West Pointe, N.Y. 19486): a cytotoxic crystalline antitumor antibiotic commonly used for treating Wilm's Tumor, and also in combination with other drugs for cancer of the testes and uterus, as well as melanomas and sarcomas.

Doxorubicin (e.g., "ADRIAMYCIN" by Adria Labs., Columbus, Ohio 43216): one of the most commonly used cytotoxic drugs, doxorubicin is an antitumor antibiotic commonly used for treating bladder, breast, head, neck, liver, lung, ovarian, prostatic, stomach, testicular and thyroid cancer, as well as Hodgkin's disease, leukemia, Wilm's tumor, lymphomas and sarcomas.

DTIC (e. g., "DACARBAZINE" by Miles Inc., West Haven, Conn. 06516): an alkylating agent commonly used in treatment of metastatic malignant melanoma and Hodgkin's disease.

Etoposide (VP-16, e.g., "VEPESID" by Bristol-Myers, Evansville, Ind. 47721): a cytotoxic epipodophyllotoxin (podophyllotoxin derivative from the mandrake plant) commonly used for treating carcinoma of the lung & testes.

Fludarabine phosphate (e.g., "FLUDARA" by Berlex Labs., Richmond, Calif. 94804): Fludarabine phosphate is a purine analog antimetabolic commonly used in the treatment of chronic lymphocytic leukemia (CLL). Other purine analogs such as 6-MP, 6-TG, azathiprine, allopurinol, acyclovir, gancylovir, deoxycoformycin, and arabinosyladienine (ara-A) have also been shown to have medical use and may also be suitable for use in the invention.

5-FU (5-fluorocytosine, e.g., "FLUOROURACIL" by Roche Labs., a division of Hoffman-LaRoche, Inc., Nutley, N.J. 07110): a cytotoxic fluoropyrimidine antimetabolic commonly used in the palliative management of carcinoma of the colon, rectum, breast, ovarian, cervix, bladder, stomach, liver and pancreas, 5-FU has synergistic interaction with other antineoplastic agents, interferons, and irradiation and is thus commonly used in combination therapy.

Floxuridine (e.g., "FUDR" by Roche Labs., a division of Hoffman-LaRoche, Inc., Nutley, N.J. 07110): a cytotoxic drug commonly used in the palliative management of gastrointestinal adenocarcinoma metastatic to the liver. Also used for treating brain, breast, head and neck cancers with liver metastases.

Hydrea (Hydroxyurea, e.g., by E. R. Squibb & Sons, Princeton, N.J. 08543): a cytotoxic drug with demonstrated tumor response for melanoma, CML (chronic myelogenous leukemia) and recurrent metastatic carcinoma of the ovary.

Idamycin (Idarubicin, e.g., by Adria Labs., Columbus, Ohio 43216): a cytotoxic antitumor antibiotic commonly used in combination with other antileukemic drugs in treatment of acute myeloid leukemia in adults (most commonly Ara-C).

Ifosfamide (e.g., "IFEX" by Bristol-Myers Oncology, a Bristol-Myers company, Evansville, Ind. 47721): an alkylating agent commonly used in combination with other approved antineoplastic agents for third line chemotherapy of testicular cancer.

Levamisole (teramisole, e.g., "ERGAMISOLE" by Janssen Pharmaceuticals, Titusville, N.J. 08560): an immunomodulator/immunopotentiator; commonly used in combination with 5-FU after surgical resection in Dukes' stage C (tumor-node-metastasis stage III) colon cancer.

Mechlorethamine hydrochloride (nitrogen mustard, e.g., "MUSTARGEN" by Merck Sharp & Dohme, West Pointe, N.Y., 19486): a cytotoxic drug formerly used as a vesicant in chemical warfare, mechloretamine hydrochloride is an alkylating agent commonly used for treating lung carcinoma; chronic lymphocytic leukemia; chronic myelocytic leukemia; Hodgkin's lymphoma; non-Hodgkin's lymphoma; malignant effusions; and mycosis fungoides.

Medroxyprogesterone (e.g., "DEPO-PROVERA" by Upjohn Co., Kalamazoo, Mich. 49001): a hormone commonly used to control abnormal uterine bleeding due to hormonal imbalance, and in adjunctive therapy and palliative treatment of inoperable, recurrent, and metasiatic endometrial or renal carcinoma.

Megestrol Acetate (progestogen, e.g., "MEGACE" by Bristol-Myers Oncology, a Bristol-Myers company, Evansville, Ind. 47721): a hormone commonly used to treat metasiatic breast cancer.

Melphalan (e.g., "ALKERAN" by Burroughs Wellcome, Research Triangle Park, N.C. 27709): a derivative of mechlorethamine hydrochloride, melphalan is an alkylating agent commonly used for treating the palliative treatment of multiple myeloma and non-resectable epithelial carcinoma of the ovary.

Mesna (e.g., "MESNEX" by Bristol-Myers Oncology, a Bristol-Myers company, Evansville, Ind. 47721): commonly used as a prophylactic agent in reducing the incidence of ifosfamide-induced hemorrhagic cystitis.

Mito-C (Mitomycin-C, e.g., "MUTAMYCIN" by Bristol-Myers Oncology, a Bristol-Myers company, Evansville, Ind. 47721): an antitumor antibiotic that functions as a cytotoxic alkylating agent, mito-C is commonly used for treating gastric carcinoma and pancreatic carcinoma.

Octreotide acetate (an octapeptide analog of somatostatin, e.g., "SANDOSTATIN" by Sandoz Pharmaceuticals, East Hanover, N.J. 07936): a biological response modifier commonly used in metasiatic carcinoid tumors, vasoactive intestinal peptide tumors, and as a reducing growth hormone.

Paraplatin (e.g., "CARBOPLATIN" by Bristol-Myers Oncology, a Bristol-Myers company, Evansville, Ind. 47721): a platinum analog commonly used in palliative treatment of ovarian carcinoma as a single agent or in combination with other chemotherapy drugs.

Prednisone (e.g., by Schering Corp., Kenilworth, N.J. 07033): a hormone commonly used for treating nervous system disorders, GI disorders, edematous states, neoplastic diseases, hematological diseases, respiratory diseases, endocrine disorders, rheumatic disorders, collagenic diseases, dermalogical diseases, opthalmic diseases and allergic states, tuberculosis, and tricamonis.

Retinoic acid (e.g., isotretinoin or "ACCUTANE" by Roche Labs., a division of Hoffman-LaRoche, Inc., Nutley, N.J. 07110): commonly used for treating treatment of severe recalcitrant nodular acne that has been unresponsive to conventional treatments, i.e., antibiotics, etc. Retinoic acid is not a cytotoxic drug.

Streptozocin (e.g., "ZANOSAR" by Upjohn, Kalamazoo, Mich. 49001): a cytotoxic drug commonly used for treating pancreatic carcinoma.

Tamoxifen (tamoxifen citrate, e.g., "NOLVADEX" by ICI Pharma, Wilmington, Del. 19897): a cytotoxic drug commonly used for treating breast carcinoma in postmenopausal women with positive estrogen receptor assay.

Taxol (e.g., "PACLITAXEL" by Bristol-Myers Oncology, a Bristol-Myers company, Evansville, Ind. 47721): a cytotoxic drug taken from the bark of the pacific yew and commonly used for treating the treatment of metasiatic carcinoma of the ovary after failure of first-line or subsequent chemotherapy.

Thio-TEPA (triethylencthiophosphoramide, e.g., "PARENTERAL" by Lederle): an alkylating agent commonly used for treating carcinoma of the bladder, breast and ovaries; Hodgkin's lymphoma; non-Hodgkin's lymphoma; and malignant effusions.

VBL (Vinblastine, e.g., "VELSAR" by Quad Pharmaceuticals, Inc., Indianapolis, Ind. 46268): a cytotoxic vinca alkaloid from the periwinkle plant commonly used for treating breast carcinoma; testicular carcinoma; Hodgkin's lymphoma; non-Hodgkin's lymphoma; mycosis fungoides; and trophoblastic tumors.

VCR (Vincristine, e.g., "VINCASAR" by Quad Pharmaceuticals, Inc., Indianapolis, Ind. 46268): a cytotoxic vinca alkaloid related to vinblastine and vindesine (desacetyl/vinblastine amide). Commonly used for treating Ewing's sarcoma; acute lymphocytic leukemia; Hodgkin's lymphoma; non-Hodgkin's lymphoma; neuroblastoma; soft tissue carcinomas; and Wilm's tumor.

Flow Cytometer: In common flow cytometers, a cell suspension is hydrodynamically forced into a stream wherein cells pass by a focal point one by one. A laser is focused upon this focal point, and as a cell passes in front of the laser, the laser light is scattered in a variety of directions. The scattered light is collected and amplified by collection optics/detectors and converted into electrical impulses. The electrical impulses can then be decoded by computer and analyzed to convey information about the cells. The flow cytometer can count the cells in the suspension and collect information on different characteristics of the cells within the suspension by detecting dyes and other markers with which the cells have been treated. For example, cell subpopulations may be excluded from certain flow cytometric analyses by marking the subpopulations and having the flow cytometer gate (subtract) them from the analysis. Despite the foregoing description of the construction and operation of a flow cytometer, it is understood that the invention may use any type of cytometer that duplicates the essential functions of the flow cytometer described. The flow cytometer utilized in the invention is the FACSCAN Immunocytometry Systems flow cytometer (Becton Dickinson, Mountain View, Calif., U.S.A.) running Consort 30 flow cytometry software (also by Becton Dickinson). Recently, the Becton Dickinson CELLQUEST software run on a MACINTOSH QUADRA 650 has been used as the preferred flow cytometry analysis software for the invention. Other suitable flow cytometers are the Coulter XL (Coulter Electronics, Hialeah, Fla., U.S.A.) or the Ortho Cytron (Ortho Diagnostic Systems, Raritan, N.J., U.S.A.).

Tumor: Throughout this specification, the term "tumor" is understood to mean cancer cells or a collection of cancer cells, whether in solid or liquid form. Examples of the tumors which have been treated or tested by use of the invention are: bladder cancer; breast cancer; colon carcinoma; non-small cell lung cancer; pancreatic cancer; liver cancer (metastases); prostatic carcinoma; acute myeloid leukemia; chronic myelogenous leukemia; chronic lymphocytic leukemia; hepatocellular carcinoma; glioblastoma; non-Hodgkin's lymphoma; melanoma; osteogenic sarcoma; ovarian carcinoma; pleomorphic adenocarcinoma; and Waldenstrom's macroglobulinemia. All have responded to treatment with the procedure. It is expected that other tumors will be treated with the procedure as they are encountered.

PHARMACOSENSITIVITY ASSAY

The pharmacosensitivity assay provides an accurate in vitro indication of in vivo tumor response within 48–96 hours from the time a solid or liquid tumor specimen is obtained from the patient. To summarize the assay procedure, a cell suspension is prepared from a patient's tumor specimen. The viable cell count of the suspension is calculated and standardized to a desired level. Multiple sample tubes are prepared, each containing cell suspension and a drug against which the pharmacosensitivity of the tumor is to be tested. Negative control tubes containing cell suspension and positive control tubes containing cell suspension and a cytotoxic agent are also prepared. The sample and control tubes are then incubated. After incubation, dyes such as propidum iodide are added to the sample and control tubes and all tubes are run through a flow cytometer. If desired, the flow cytometer can be compensated beforehand to factor out the presence of white cells in the cell suspension by staining the cleukouspension with leukocyte-binding substances such as fluorescein-labeled monoclonal antibodies, analyzing the stained cell suspension in the flow cytometer, and using the results to gate the white cells from further analyses. The flow cytometer may count the apoptotic cells (or alternatively, the non-apoptotic cells if the appropriate dye is used) and thereby obtain a measure of the cell kill, i.e., the pharmacosensitivity of the tumor cells.

(1) MATERIALS

The following materials are recommended for the performance of the pharmacosensitivity assay of the treatment method:

Laminar flow hood
RPMI medium (IX)
Patient culture medium
Tissue culture transport medium
Select-a-Perle pipetter
Select-a-Pette tips
Eppendorf pipers
Eppendorf Combitips (2.5 ml, 5.0 ml, 12.5 ml)
Falcon 2072 plastic test tubes (with caps for FACS analysis)
15 ml capped tubes
100×15 mm sterile petri dishes
50 ml capped conical tubes
Homogenizer
Trypan blue stain (0.4%)
Hemocytometer with cover slips
Microscopes (with light)
Hand tally counter
Histopaque 1077
Pipet suction aid
Refrigerated centrifuge
$CO_2$ incubator
Drugs (lists provided elsewhere in specification)
Vortex mixer
Refrigerator (2°–10° C.)
Scalpel
Sharps container
Propidium iodide (Sigma P4170) (Sigma, St. Louis, Mo., U.S.A.)
Phosphate buffered saline, ph 7.2 (PBS)
Flow cytometer (FACScan) (Becton Dickinson, Mountain View, Calif., U.S.A.)
Clay-Adams Sero-fuge II (Clay-Adams, Parsippany, N.J., U.S.A.)
CD45-FITC labeled MAb
Anti-cytokeratin-FITC labeled MAb
FACSlyse (diluted 1 in 10 in deionized water) (Becton Dickinson, Mountain View, Calif., U.S.A.)
All equipment is sterilized where appropriate.

(2) REAGENT PREPARATION

The procedure utilizes several reagents, the preparation of which is described below.

Preparation of 0.05 mg/ml Propidium Iodide Reagent (components available from Gibco, Grand Island, N.Y., U.S.A.)

2.5 milligrams (mg) propidium iodide is added to 50 milliliters (ml) phosphate buffered saline (PBS), pH 7.2, in a 50 ml tube. The tube is gently mixed by inverting the tube several times. The tube is labeled with the date of preparation and the expiration date and stored at 4° C. Since propidium iodide is light sensitive, the tube should be wrapped in foil before storage. The propidium iodide reagent is stable for approximately one month.

Preparation of Patient Culture Medium (IMDM/RPMI 1640 (1×), 10% FBS) (components available from Sigma, St. Louis, Mo., U.S.A.)

| AMOUNT | COMPONENT |
|---|---|
| 500.0 ml | RPMI Medium 1640 (1X), liquid with L-Glutamine |
| 500.0 ml | Iscove's Modified Dulbecco's Medium (IMDM) (1X), liquid with L-Glutamine with 25 mM HEPES buffer with 3,024 mg/L sodium bicarbonate without alpha-thioglycerol without beta-mercaptoethanol |
| 100.0 ml | Fetal Bovine Serum (FBS) |
| 10.0 ml | L-Glutamine - 200 mM (100X), liquid |
| 10.0 ml | Penicillin-Streptomycin, liquid 10,000 units/ml Penicillin 10,000 µg/ml Streptomycin |
| 5.0 ml | NEAA Mixture 100x |
| 5.0 ml | MEM Vitamin Solution 100x |
| 5.0 ml | Insulin-Transferrin-Sodium Selenite Media Supplement |

250.0 ml of RPMI (1×) and 250.0 ml of IMDM in sterile graduated cylinders are added under a sterile laminar flow hood to a 500.0 ml sterile filter system with a 0.22 mm cellulose acetate membrane with a 60 mm prefilter. FBS is added with sterile disposable pipettes. All other ingredients listed are to be added immediately prior to use. Phenol red is used to perform a visual check of medium color for appropriate pH. The prepared medium is stable for 3 months when refrigerated at 2°–8° C.

Preparation of RPMI 1640 Medium (1×) (10% RPMI 1640 (1×) G,G fortified) (components available from Sigma, St. Louis, Mo., U.S.A.)

| AMOUNT | COMPONENT |
| --- | --- |
| 500.0 ml | RPMI Medium 1640 (1X), liquid with L-Glutamine |
| 50.0 ml | Fetal Bovine Serum |
| 5.0 ml | Penicillin-Streptomycin, liquid 10,000 units/ml Penicillin 10,000 μg/ml Streptomycin |
| 5.0 ml | L-Glutamine - 200 mL (100x), liquid |
| 5.0 ml | Insulin-Transferrin-Sodium Selenite Media Supplement |

All components are combined and thoroughly mixed under a sterile laminar flow hood. Phenol red is used to perform a visual check of medium color for appropriate pH. The prepared medium is stable for 3 months when refrigerated at 2°–8° C.

Preparation of Tissue Culture Transport Medium (RPMI 1640 (1×) 15% FBS) (components available from Sigma, St. Louis, Mo., U.S.A.)

| AMOUNT | COMPONENT |
| --- | --- |
| 500.0 ml | RPMI Medium 1640 (1X), liquid |
| 75.0 ml | Fetal Bovine Serum |
| 5.0 ml | Penicillin-Streptomycin, liquid 10,000 units/ml Penicillin 10,000 μg/ml Streptomycin |
| 5.0 ml | L-Glutamine - 200 mM (100x), liquid |

All components are combined and thoroughly mixed under a sterile laminar flow hood. Phenol red is used to perform a visual check of medium color for appropriate pH. The medium is aliquotted into 50 ml conical tubes in 20.0 ml amounts. The prepared medium is stable for 3 months when refrigerated at 2°–8° C.

(3) PREPARATION OF THE CELL SUSPENSION

The pharmacosensitivity assay may use tumor samples from any type of tumor, including solid tumors obtained during surgery or biopsy, bone marrow aspirates and trephines, ascitic fluid, pleural fluid, and other types of tumor samples. After the tumor is obtained and placed in tissue culture transport medium, the tumor sample is converted to a cell suspension upon which the steps of the assay are performed. The sample is preferably large enough that it can yield an optimum of 15 ml of $1\times10^6$ viable tumor cells per ml of cell suspension, the preparation of which is described below.

For a solid tumor, the following steps are taken to prepare the cell suspension. The tumor specimen is cut into pea-size portions in a sterile petri dish using a sterile scalpel and forceps. The original tissue culture transport medium is retained for later use. The tumor portions are placed in a glass conical tube that has a matched loose-fitting homogenizer. 5.0 ml of tissue culture transport medium is added. The tumor portions are then gently homogenized and transferred to a sterile 50 ml conical tube. When all of the tumor portions have been homogenized, the mixture is stirred well and allowed to settle undisturbed for one minute to allow clumps of tissue to settle out. The supernatant is pipetted into a sterile tube, diluted with patient culture and centrifuged at 1600 RPM for 5 minutes. The supernatant is removed and the cells are resuspended in RPMI 1640 (1×) medium.

For liquid tumor, such as ascites, bone marrow, etc., monocyte separation may be performed by density gradient centrifugation on Ficoll-Hypaque medium (Pharmacia, Dublin, Ohio, U.S.A.). 20–25 ml of Histopaque 1077 is placed in the appropriate number of capped sterile 50 ml conical cubes by use of a sterile pipet. Using another sterile pipet, the liquid tumor is gently layered at a 45 degree angle onto the histopaque using a 1:1 ratio of histopaque to specimen. The histopaque is then centrifuged at 1600 RPM for 20 minutes in a refrigerated centrifuge at 4° C. (brake on 2). The supernatant is then removed and discarded, and the cell interface is removed and placed in RPMI 1640 (1×) medium in a pre-labeled tube. The cells should be diluted with the RPMI 1640 (1×) medium quickly because the histopaque is toxic to the cells if left on them for extended periods of time. The cells are then washed twice with RPMI 1640 (1×) medium and centrifuged at 1600 RPM for 5 minutes (brake on 2). The supernatant is removed and discarded, and the cell pellet is resuspended in 5.0 ml of RPMI 1640 (1×) medium.

Solid tumors are sometimes very hard and difficult to homogenize. If that is the case, it has been found that the procedure set out above for liquid tumors can be used to recover more viable cells and to rid the culture of debris and/or red blood cells.

(4) ANALYSIS OF VIABLE CELL CONCENTRATION

In this step of the procedure, the percentage of viable tumor cells is measured using viability tests known to the art, such as the Trypan Blue test or the MTT test. In the preferred method, 0.1 ml of well-mixed cell suspension, 0.2 ml of 0.4% Trypan Blue stain, and 0.7 ml of patient culture medium are combined in a 12×75 ml glass tube to obtain a 1:10 dilution of the cell suspension. The cell suspension is mixed well and charged into one chamber of a hemocytometer. A light microscope is used to count the both the viable tumor cells (those which have not absorbed the Trypan Blue) and the total number of tumor cells (stained and unstained) in the four corner 1 $mm^2$ squares.

The viable cell count is then determined using the following equation:

Viable cell count = [Average # of viable cells per square] ×

[dilution factor (here, 10)] ×

[hemocytometer multiplication factor]

The total cell count can be similarly calculated, and used in conjunction with the viable cell count to calculate the percent viability of the cell suspension according to the following formula:

% Viability=[viable cell count/total cell count]×100%

As noted above, other viability tests such as the MTT test may be used in place of the Trypan Blue exclusion test.

(5) ADJUSTMENT OF VIABLE CELL CONCENTRATION

A viable cell concentration of $1\times10^6$ viable tumor cells per ml of cell suspension is preferred for the use in the assay because the drug aliquots used in the procedure are predicated on a base viable tumor cell concentration of $1\times10^6$ viable tumor cells per ml of cell suspension. Where a concentration of greater than $1\times10^6$ viable tumor cells per ml is present, the cell suspension is diluted with patient culture medium to yield this concentration. The dilution is performed according to the following formula:

Final cell suspension volume = [starting cell suspension volume] × [starting cell concentration] ÷ [desired concentration (here 1 × 10⁶)]

Patient medium is added to reach the calculated final cell suspension volume. Alternatively, if the viable cell concentration is below 1×10⁶ viable tumor cells per ml of cell suspension, the drug aliquots are diluted accordingly as described below at step (7). This drug aliquot dilution step may be performed at this stage instead, if desired.

(6) PREPARATION OF CONTROL SAMPLES 0.8 ml of patient culture medium is added to each of three sterile 75×12 mm Falcon 2072 plastic tubes (each having a cap for flow cytometric analysis). 0.2 ml of cell suspension is added to each of these tubes, which are to be used as negative control samples.

A positive control sample is also prepared. The preparation of this positive control sample will be outlined below.

(7) PREPARATION OF DRUG SAMPLES

One sterile 75×12 mm Falcon 2072 plastic tube (having a cap for flow cytometric analysis) is labeled for each drug to be used in the test. An additional tube is labeled as a positive control tube. The tubes are preset by adding 0.1 ml of the appropriate drug solution (at the aliquot amount set out below) and 0.7 ml of patient medium. These preset tubes may be stored at 4° C. for 7 days if capped with sterile caps.

(a) Drug Solution Aliquots for Use in the Drug Samples: following is a list of exemplary drugs used in the procedure and the preferred aliquot amount for their use.

Abrin (used in positive control sample): The preferred cytotoxic agent for use in the positive control is abrin (toxalbumin). Abrin solution is prepared by diluting abrin with RPMI 1640 (1×) medium to a working concentration of 0.5 mg/ml. As noted above, 0.1 ml of this abrin solution is added to the positive control tube.

Amethopterin: is generally supplied as a sterile lyophilized powder. The powder is reconstituted with sterile distilled water to obtain a 25.0 mg/ml concentration, and then dissolved in RPMI 1640 (1×) medium to yield a final working concentration of 0.25 mg/3.0 ml. If pre-prepared, the amethopterin solution may be stored at room temperature. As noted above, the amethopterin drug sample tube is prepared by adding 0.1 ml of amethopterin solution to a drug tube.

Ara-C: is generally supplied as a sterile lyophilized powder. The powder is reconstituted with sterile distilled water to obtain a 20.0 mg/ml concentration, and then dissolved in RPMI 1640 (1×) to obtain a final working concentration of 0.60 mg/ml. If pre-prepared, the Ara-C solution may be stored at room temperature. As noted above, the Ara-C drug sample tube is prepared by adding 0.1 ml of Ara-C solution to a drug tube.

BCNU: is generally supplied as a sterile lyophilized powder. The powder is reconstituted with sterile distilled water to obtain a 3.3 mg/ml concentration, and then dissolved in RPMI 1640 (1×) medium to yield a final working concentration of 0.003 mg/3.0 ml. If pre-prepared, the BCNU solution may be stored in the refrigerator. As noted above, the BCNU drug sample tube is prepared by adding 0.1 ml of BCNU solution to a drug tube.

Bleomycin: is generally supplied as a sterile lyophilized powder. The powder is reconstituted with sterile distilled water to obtain a 5.0 u/ml concentration, and then dissolved in RPMI 1640 (1×) medium to yield a final working concentration of 0.05 u/ml. If pre-prepared, the bleomycin solution may be stored in the refrigerator. As noted above, the bleomycin drug sample tube is prepared by adding 0.1 ml of bleomycin solution to a drug tube.

Cis-platin: is generally supplied as a sterile lyophilized powder. The powder is reconstituted with sterile distilled water to obtain a 1.0 mg/ml concentration, and then dissolved in RPMI 1640 (1×) medium to yield a final working concentration of 0.03 mg/3.0 ml. If pre-prepared, the cis-platin solution may be stored at room temperature. As noted above, the cis-platin drug sample tube is prepared by adding 0.1 ml of cis-platin solution to a drug tube.

Cladribine: is generally supplied in 1.0 mg/ml vials. The cladribine is dissolved in RPMI 1640 (1×) medium to yield a final working concentration of 0.01 mg/ml. If pre-prepared, the cladribine solution may be stored in the refrigerator. As noted above, the cladribine drug sample tube is prepared by adding 0.1 ml of cladribine solution to a drug tube.

Cyclophosphamide: is generally supplied as a sterile lyophilized powder. The powder is reconstituted with sterile distilled water to obtain a 20.0 mg/ml concentration, and then dissolved in RPMI 1640 (1×) medium to yield a final working concentration of 0.020 mg/3.0 ml. If pre-prepared, the cyclophosphamide solution may be stored in the refrigerator. As noted above, the cyclophosphamide drug sample tube is prepared by adding 0.1 ml of cyclophosphamide solution to a drug tube.

Dactinomycin: is generally supplied as a sterile lyophilized powder. The powder is reconstituted with sterile distilled water to obtain a 0.5 mg/ml concentration, and then solved in RPMI 1640 (1×) medium to yield a final working concentration of 0.015 mg/ml. If pre-prepared, the dactinomycin solution may be stored at room temperature. As noted above, the dactinomycin drug sample tube is prepared by adding 0.1 ml of dactinomycin solution to a drug tube.

Doxorubicin: is generally supplied as a sterile lyophilized powder. The powder is reconstituted with sterile distilled water to obtain a 2.0 mg/ml concentration, and then dissolved in RPMI 1640 (1×) to yield a final working concentration of 0.02 mg/3.0 ml. If pre-prepared, the doxorubicin solution should be stored in the refrigerator. As noted above, the doxorubicin drug sample tube is prepared by adding 0.1 ml of doxorubicin solution to a drug tube.

DTIC: is generally supplied as a sterile lyophilized powder. The powder is reconstituted with sterile distilled water to obtain a 10.0 mg/ml concentration, and then dissolved in RPMI 1640 (1×) medium to yield a final working concentration of 0.1 mg/3.0ml. If pre-prepared, the DTIC solution may be stored at room temperature. As noted above, the DTIC drug sample robe is prepared by adding 0.1 ml of DTIC solution to a drug tube.

Etoposide: is generally supplied in either liquid or capsule form. The etoposide is dissolved in RPMI 1640 (1×) medium to yield a final working concentration of 0.20 mg/3.0 ml. If pre-prepared, the etoposide solution may be stored at room temperature. As noted above, the etoposide drug sample tube is prepared by adding 0.1 ml of etoposide solution to a drug tube.

Fludarabine phosphate: is generally supplied as a sterile lyophilized powder. The powder is reconstituted with sterile distilled water to obtain a 25.0 mg/ml concentration, and then dissolved in RPMI 1640 (1×) medium to yield a final working concentration of 0.25 mg/3.0 ml. If pre-prepared, the fludarabine phosphate solution may be stored in the refrigerator. As noted above, the fludarabine phosphate drug sample tube is prepared by adding 0.1 ml of fludarabine phosphate solution to a drug tube.

5-FU: is generally supplied as an injectable solution with a concentration of 50.0 mg/ml. RPMI 1640 (1×) medium is added to obtain a working concentration of 0.50 mg/3.0 ml. If pre-prepared, the 5-FU solution may be stored at room temperature. As noted above, the 5-FU drug sample tube is prepared by adding 0.1 ml of 5-FU solution to a drug tube.

Floxuridine: is generally supplied as a powder. The powder is reconstituted with sterile distilled water to obtain a 100.0 mg/ml concentration, and then dissolved in RPMI 1640 (1×) medium to yield a final working concentration of 0.2 mg/3.0 ml. If pre-prepared, the floxuridine solution may be stored in the refrigerator. As noted above, the floxuridine drug sample tube is prepared by adding 0.1 ml of floxuridine solution to a drug tube.

G-CSF: If supplied in lyophilized form, the G-CSF should be reconstituted following the manufacturer's instructions. Stock solution concentration may be variable. The G-CSF should be diluted with RPMI (1×) medium to obtain a working concentration of 200.0 u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

GM-CSF: If supplied in lyophilized form, the GM-CSF should be reconstituted following the manufacturer's instructions. Stock solution concentration may be variable. The GM-CSF should be diluted with RPMI (1×) medium to obtain a working concentration of 62.5 u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

Hydrea: is generally supplied as 500 mg capsules. The capsules are reconstituted with sterile distilled water to obtain a 50 mg/ml concentration, and then dissolved in RPMI 1640 (1×) medium to yield a final working concentration of 0.50 mg/ml. If pre-prepared, the hydrea solution may be stored at room temperature. As noted above, the hydrea drug sample tube is prepared by adding 0.1 ml of hydrea solution to a drug tube.

Idamycin: is generally supplied as a sterile lyophilized powder. The powder is reconstituted with sterile distilled water to obtain a 1.0 mg/ml concentration, and then dissolved in RPMI 1640 (1×) medium to yield a final working concentration of 0.001 mg/3.0 ml. If pre-prepared, the idamycin solution may be stored at room temperature. As noted above, the idamycin drug sample tube is prepared by adding 0.1 ml of idamycin solution to a drug tube.

Ifosfamide: is generally supplied as a sterile lyophilized powder. The powder is reconstituted with sterile distilled water to obtain a 50.0 mg/ml concentration, and then dissolved in RPMI 1640 (1×) medium to yield a final working concentration of 1.5 mg/ml. If pre-prepared, the ifosfamide solution may be stored in the refrigerator. As noted above, the ifosfamide drug sample tube is prepared by adding 0.1 ml of ifosfamide solution to a drug tube.

Levamisole: is generally supplied in 10.0 mg tablets. The tablets are reconstituted with sterile distilled water to obtain a 5.0 mg/ml concentration, and then dissolved in RPMI 1640 (1×) medium to yield a final working concentration of 0.05 mg/3.0 ml. If pre-prepared, the levamisole solution may be stored at room temperature. As noted above, the levamisole drug sample tube is prepared by adding 0.1 ml of levamisole solution to a drug tube.

Mechlorethamine hydrochloride: is generally supplied as a sterile lyophilized powder. The powder is reconstituted with sterile distilled water to obtain a 1.0 mg/ml concentration, and then dissolved in RPMI 1640 (1×) medium to yield a final working concentration of 0.01 mg/3.0 ml. If pre-prepared, the mechlorethamine solution may be stored at room temperature. As noted above, the mechlorethamine drug sample tube is prepared by adding 0.1 ml of mechlorethamine solution to a drug tube.

Medroxyprogesterone: is generally supplied as a sterile lyophilized powder. The powder is reconstituted with sterile distilled water to obtain a 150.0 mg/ml concentration, and then dissolved in RPMI 1640 (1×) medium to yield a final working concentration of 1.50 mg/3.0 ml. If pre-prepared, the medroxyprogesterone solution may be stored at room temperature. As noted above, the medroxyprogesterone drug sample tube is prepared by adding 0.1 ml of medroxyprogesterone solution to a drug tube.

Megestrol acetate: is generally supplied in tablet form. The tablets are reconstituted with sterile distilled water to obtain a 4.0 mg/ml concentration, and then dissolved in RPMI 1640 (1×) medium to yield a final working concentration of 0.008 mg/3.0 ml. If pre-prepared, the megestrol acetate solution may be stored at room temperature. As noted above, the megestrol acetate drug sample tube is prepared by adding 0.1 ml of megestrol acetate solution to a drug tube.

Melphalan: is generally supplied in 2.0 mg tablets. The tablets are reconstituted with sterile distilled water to obtain a 0.2 mg/ml concentration, and then dissolved in RPMI 1640 (1×) medium to yield a final working concentration of 0.0002 mg/3.0 ml. If pre-prepared, the melphalan solution may be stored in the refrigerator. As noted above, the melphalan drug sample tube is prepared by adding 0.1 ml of melphalan solution to a drug tube.

Mesna: is generally supplied in prepared vials. The mesna is dissolved in RPMI 1640 (1×) medium to yield a final working concentration of 3.0 mg/3.0 ml. If pre-prepared, the mesna solution may be stored in the refrigerator. As noted above, the mesna drug sample tube is prepared by adding 0.1 ml of mesna solution to a drug tube.

Mito-C: is generally supplied in 0.5 mg/ml vials. The mito-C is dissolved in RPMI 1640 (1×) medium to yield a final working concentration of 0.005 mg/ml. If pre-prepared, the mito-C solution may be stored at room temperature. As noted above, the mito-C drug sample robe is prepared by adding 0.1 ml of mito-C solution to a drug tube.

nHuIFNα: If supplied in lyophilized form, the nHuIFNα should be reconstituted following the manufacturer's instructions. Stock solution concentration may be variable. The nHuIFNα should be diluted with RPMI (1×) medium to obtain a working concentration of $1.0 \times 10^3$ u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

nHuIFNβ: If supplied in lyophilized form, the nHuIFNβ should be reconstituted following the manufacturer's instructions. Stock solution concentration may be variable. The nHuIFNβ should be diluted with RPMI (1×) medium to obtain a working concentration of $1.0 \times 10^3$ u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

nHuIFNπ: If supplied in lyophilized form, the nHuIFNπ should be reconstituted following the manufacturer's instructions. Stock solution concentration may be variable. The nHuIFNπ should be diluted with RPMI (1×) medium to obtain a working concentration of $5.0 \times 10^2$ u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

Octreotide acetate: is prepared similarly to somatostatin, discussed below.

Paraplatin: is generally supplied as a sterile lyophilized powder. The powder is reconstituted with sterile distilled water to obtain a final concentration of 5.0 mg/ml, and then dissolved in RPMI 1640 (1×) medium to yield a final working concentration of 0.05 mg/ml. If pre-prepared, the paraplatin solution may be stored at room temperature. As noted above, the paraplatin drug sample tube is prepared by adding 0.1 ml of paraplatin solution to a drug tube.

Prednisone: is generally supplied in liquid form. The prednisone is dissolved in RPMI 1640 (1×) medium to yield a final working concentration of 0.6 mg/ml. If pre-prepared, the prednisone solution may be stored at room temperature. As noted above, the prednisone drug sample tube is prepared by adding 0.1 ml of prednisone solution to a drug tube.

Retinoic acid: is generally available in tablet form. The tablets are dissolved in RPMI 1640 (1×) medium to obtain a final working concentration of 0.04 mg/3.0 ml. If pre-prepared, the retinoic acid solution may be stored at room temperature. As noted above, the retinoic acid drug sample tube is prepared by adding 0.1 ml of retinoic acid solution to a drug tube.

rIFNα-2a: If supplied in lyophilized form, the rIFNα-2a should be reconstituted following the manufacturer's instructions. Stock solution concentration may be variable. The rIFNα-2a should be diluted with RPMI (1×) medium to obtain a working concentration of 30,000 u/ml. Sterility should be maintained throughout the preparation process. Working solutions may be prepared as needed in 17×100 sterile capped tubes. Frozen dilutions are stable up to five years at −20° C. Subsequent dilutions of frozen stock dilutions cannot exceed the expiration date of the frozen stock solution. Thawed aliquots are stable for three months at 2°–8° C.

rIFNα-2b: If supplied in lyophilized form, the rIFNα-2b should be reconstituted following the manufacturer's instructions. Stock solution concentration may be variable. The rIFNα-2b should be diluted with RPMI (1×) medium to obtain a working concentration of 1,000 neutralizing units/ml. Sterility should be maintained throughout the preparation process. Working solutions may be frozen in 3.5 ml aliquots in 12×75 sterile capped tubes. Frozen dilutions are stable up to five years at −20° C. Subsequent dilutions of frozen stock dilutions cannot exceed the expiration date of the frozen stock solution. Thawed aliquots are stable for three months at 2°–8° C.

rIFNβ-1b: If supplied in lyophilized form, the rIFNβ-1b should be reconstituted following the manufacturer's instructions. Stock solution concentration may be variable. The rIFNβ-1b should be diluted with RPMI (1×) medium to obtain a working concentration of $1.0 \times 10^3$ u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

rIFNτ-1b: If supplied in lyophilized form, the rIFNτ-1b should be reconstituted following the manufacturer's instructions. Stock solution concentration may be variable. The rIFNτ-1b should be diluted with RPMI (1×) medium to obtain a working concentration of 0.01 μg/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

rIL-2: If supplied in lyophilized form, the rIL-2 should be reconstituted following the manufacturer's instructions. Stock solution concentration may be variable. The rIL-2 should be diluted with RPMI (1×) medium to obtain a working concentration of 10.0 u/ml. Sterility should be maintained throughout the preparation process. Working solutions may be frozen in 10 ml aliquots in 17×100 sterile capped tubes. Frozen dilutions are stable up to five years at −20° C. Subsequent dilutions of frozen stock dilutions cannot exceed the expiration date of the frozen stock solution. Thawed aliquots are stable for three months at 2°–8° C.

rTNF: If supplied in lyophilized form, the rTNF should be reconstituted following the manufacturer's instructions. Stock solution concentration may be variable. The rTNF should be diluted with RPMI (1×) medium to obtain a working concentration of $1.2 \times 10^2$ u/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

Somatostatin: If supplied in lyophilized powder form, the Somatostatin should be reconstituted following the manufacturer's instructions. Stock solution concentration may be variable. The somatostatin should be diluted with RPMI (1×) medium to obtain a working concentration of 50.0/µg/ml. Sterility should be maintained throughout the preparation process. Working solutions may be frozen in 1.5 ml aliquots in sterile nalgene cryovials. Frozen dilutions are stable up to five years at −20° C. Subsequent dilutions of frozen stock dilutions cannot exceed the expiration date of the frozen stock solution. Thawed aliquots are stable for three months at 2°–8° C.

If supplied in liquid form, somatostatin is provided in 50 ug/cc vials with diluent. The somatostatin is dissolved in RPMI 1640 (1×) medium to yield a final working concentration of 5.0 ug/3.0 ml. If pre-prepared, the somatostatin solution may be stored in the refrigerator. As noted above, the somatostatin drug sample tube is prepared by adding 0.1 ml of somatostatin solution to a drug tube.

Streptozocin: is generally supplied as a sterile lyophilized powder. The powder is reconstituted with sterile distilled water to obtain a 100.0 mg/ml concentration, and then dissolved in RPMI 1640 (1×) medium to yield a final working concentration of 1.0 mg/3.0 ml. If pre-prepared, the streptozocin solution may be stored in the refrigerator. As noted above, the streptozocin drug sample tube is prepared by adding 0.1 ml of streptozocin solution to a drug tube.

Tamoxifen: is generally supplied in 10.0 mg tablets. The tablets are reconstituted with sterile distilled water to obtain a 1.0 mg/ml concentration, and then dissolved in RPMI 1640 (1×) medium to yield a final working concentration of 0.003 mg/3.0 ml. If pre-prepared, the tamoxifen solution may be stored at room temperature. As noted above, the tamoxifen drug sample tube is prepared by adding 0.1 ml of tamoxifen solution to a drug tube.

Taxol: is generally supplied as a liquid. The taxol is dissolved in RPMI 1640 (1×) medium to yield a final working concentration of 0.06 mg/3.0 ml. If pre-prepared, the taxol solution may be stored in the refrigerator. As noted above, the taxol drug sample tube is prepared by adding 0.1 ml of taxol solution to a drug tube.

Thio-TEPA: is generally supplied as a sterile lyophilized powder. The powder is reconstituted with sterile distilled water to obtain a 2.5 mg/ml concentration, and then dissolved in RPMI 1640 (1×) medium to yield a final working concentration of 0.025 mg/ml. If pre-prepared, the thio-TEPA solution may be stored in the refrigerator. As noted above, the thio-TEPA drug sample tube is prepared by adding 0.1 ml of thio-TEPA solution to a drug tube.

VBL: is generally supplied as a sterile lyophilized powder. The powder is reconstituted with sterile distilled water to obtain a 1.0 mg/ml concentration, and then dissolved in RPMI 1640 (1×) medium to yield a final working concentration of 0.03 mg/ml. If pre-prepared, the VBL solution may be stored in the refrigerator. As noted above, the VBL drug sample tube is prepared by adding 0.1 ml of VBL solution to a drug tube.

VCR: is generally supplied in liquid form. The VCR is dissolved in RPMI 1640 (1×) medium to yield a final working concentration of 0.01 mg/ml. If pre-prepared, the VCR solution may be stored in the refrigerator. As noted above, the VCR drug sample tube is prepared by adding 0.1 ml of VCR solution to a drug tube.

Additional information regarding standard aliquots and dosages for any of the aforementioned drugs may found in the most current edition of the Physician's Desk Reference. It is expected that aliquots can be prepared for other chemotherapeutic drugs as well, examples being acivin, aclacinomycin A, alanine mustard, altretamine, aminoglutethimide, aminopterin, amsacrine (mAMSA), various anabolic steroids, anthrapyrazoles, L-asparaginase, 5-axacytidine, bacillus calmette-guerin, bisantrene, buserelin, busulfan, butyryloxyethylglyoxal ditiosemicarbazone, camptothecin, carbamate ester, carzinophyllin, CCNU, chlorambucil, chlorethyl-methylcycloexyl-nitrosourea, chlorethylcyclohexylnitrosourea, chlorordeoxyadenosine, chlorotrianisene, chlorozotocin, chromic phosphate P32, chromomycin-A, cobalt proporphyrin complex, corticotropin, cyproterone acetate, daunomycin, daunorubicin, dehydroemitine, 4-demethoxydaunorubicin, demothydoxorubicin, deoxydoxorubicin, dexamethosone, dibromodulcitol, dichloromethothotrexate, diethylstilbestrol, DL-serine bis(2-chloropropyl), doxifluridine, elliptinium acetate, 4'-epidoxorubicin, epirubicin, epoetin alpha, erythropoeitin, esorubicin, estradiol, estradiol valerate, estramustine, estrogens, estrone, ethynil estradiol, etidronate, fluoxymesterone, flutamide, folic acid, fotemustine, ftorafur, 4-FU, galactitol, gallium nitrate, goserelin, hexamethylmelamine (HMM), hydrocortisone, 4-hydroperoxycyclophosphamide, hydroxyprogesterone, ICRf 159, immune globulin IGIV, L-asparaginase, leucovorin calcium, leuprolide, levadopa, levothyroxine, lindane, liothyronine, liotrix, lomustine, masoprocol, maytansine, menogaril, 6-mercaptopurine, methosalen, methylesterone, methyl-lomustine, mithracin, mithramycin, mitotane, mitoxantrone, 6 MP, nandrolone, navelbine, neocarzinostatin, nitrofururazone, ondansetrone HCl, pamidronate disodium, pentamethylmelamine (PMM), pentostatin, peptiochemio, plicamycin, prednimustine, probroman, procarbazine, profiromycin, razoxane, retinoids (retinol and retinol analogs), rubidazone, semustine, sodium iodine I-131, sodium phosphate P32, SPG 827 (podophyllin derivative), spirogermanium, streptonigrin, 6-thioguanine, tenoposide, testolactone, testosterone, 3-TGDR, thioguanine, thyroglobulin, thyrotropin, trilostane, uracil mustard, verapamil, vindesine, vinzelidine, and zinostatin. Again, standard aliquots and dosages may be prepared as stated in the Physician's Desk Reference. Of course, other chemotherapeutic agents may be used as they become available.

Safety precautions should be followed at all times when handling the drugs. Most cytotoxic drugs are deemed to be carcinogenic and are severe irritants to exposed skin. Extreme care should be taken when handling these substances and personal protective clothing should be worn at all times. Special care must be taken when handling abrin, and all material coming into contact with abrin must be autoclaved after each use.

(b) Adjustment of Drug Concentration

If the viable cell concentration of the cell suspension is less than $1\times10^6$ cells/ml, it is necessary to reduce the drug concentration in each drug sample tube by the addition of more patient culture medium. Patient culture medium is added to each tube in a logarithmic relationship to the viable cell concentration, with 1.0 ml of patient culture medium being added to each tube for each order of magnitude less than $1\times10^6$ cells/ml. The following table illustrates this relation:

| Viable Cell Concentration (cells/ml) | Volume of Patient Culture Medium Added (ml) |
|---|---|
| $1.0 \times 10^6$ | 0 |
| $7.5 \times 10^5$ | 0.25 |
| $5.0 \times 10^5$ | 0.5 |
| $2.5 \times 10^5$ | 0.75 |
| $1.0 \times 10^5$ | 1.0 |

Acceptable results may be obtained if the viable cell concentration is rounded to the closest amount listed in the table and the corresponding volume of patient culture medium is added. However, cell counts of less than $1\times10^5$/ml are not preferred.

(c) Completion of the Drug Samples

To complete the drug samples and the positive control sample, 0.2 ml of cell suspension is added to each tube.

(8) INCUBATION

The drug samples and positive and negative control samples are then mixed and incubated. An optimum incubation time and environment has been found to be 72 hours at 37° C. and 5% $CO_2$. Greater incubation times do not appear to yield significantly different results.

(9) COMPENSATION FOR WHITE CELL CONTENT OF THE SAMPLES

Because white cells present in the samples can skew the results of the flow cytometry readings, it is recommended that the flow cytometer be compensated for the white cell content of the tumor sample using the following steps. These steps need not be followed for bone marrow specimens because in that case, the white cells are the target cells to be measured.

0.2 ml of cell suspension is added to a 75×12 mm Falcon tube with 10 microliters of FITC (fluorescein isothiocyanate) labeled CD45 monoclonal antibody (MAb). The tube is incubated at room temperature for 15 minutes. 2.0 ml of FACSlyse solution (Becton Dickinson, Mountain View, Calif., U.S.A.), diluted 1:10 in deionized water, is added to the tube. The tube is again incubated at room temperature for 10 minutes. The tube is then centrifuged at high speed and the supernatant is decanted. The tube is washed once by adding 2.0 ml of PBS to the tube and centrifuging at high speed. The supernatant is decanted and 0.5 ml PBS is added.

A flow cytometer is then used to detect the FITC-marked white cells. The tube is placed on the flow cytometer and analyzed. A histogram of the FITC fluorescence versus the number of cells is created, wherein the CD45 negative population should be positioned on the far left of the histogram. The first marker is placed on the origin, the second marker is placed immediately to the right of the portion of the histogram showing the negative population, and subtraction is performed to calculate the number and percentage of non-white cells in the specimen. The following description outlines the above procedure with reference to the preferred flow cytometer and software, the FACScan running the Consort 30 program:

a. Select Consort 30 from main menu on FACScan.
b. Calibrate FSC (forward scatter), SSC (side scatter), and FL1 and FL2 (flourescence) settings.
c. Acquire and store data (press 2).
d. Place tube on cytometer.
e. Acquire data into memory (press 5).
f. Select "histogram" (press 1).
g. Exit when collection is complete (press 0).

NOTE: Since the data has not been saved, it is essential to continue with data analysis. Failure to do so will result in loss of data and the need to recollect data from the tube.

h. Analyze data (press 4).
i. Select single histogram (press 2).
j. Change parameter to FL-1 (press <shift>-1).
k. Set markers (press <shift>-3).
l. Number markers (press 2).

The CD45 negative population should be positioned on the far left of the histogram. Set marker 1 on the origin by pressing the <return> key without moving the marker. Set marker 2 immediately to the right of the negative histogram.

m. Press any key and then press <shift> 9 to print the CD45 negative count, i.e., the number of non-white cells in the specimen.

The CD45 negative population does not necessarily represent tumor cells. Normal epithelial cells, rather than tumor cells, may still be represented within this population.

It is understood that other methods known to the art for measuring the monocyte population may be used to compensate the flow cytometer, and that the method is not limited to the use of FITC-labeled CD45 MAb. As an example, another preferred detection agent is anti-cytokeratin bound to FITC or to other fluorochromes known to the art.

(10) STAINING

The drug and control tubes are removed from the incubator and centrifuged at high speed (Sero-fuge II) for 3 minutes. The supernatant is removed and the cell button is resuspended by gentle vortexing.

If the percentage of CD45-negative cells, i.e., non-white cells, is less than 80%, steps must be taken to set the compensation on the flow cytometer. 10.0 μl of FITC-labeled CD45 MAb is added to one of the negative control samples and the sample is incubated at room temperature for 15 minutes. The sample is washed once by adding 2.0 ml of PBS to the tube, centrifuging at high speed, and decanting the supernatant, and is then washed a second time by the same procedure.

0.5 ml of 0.05 mg/ml propidium iodide reagent is added to each drug sample and non-FITC-CD45 labeled control sample. All samples are then allowed to stand for a minimum of 10 minutes at room temperature. The samples should not be left for more than one hour after the addition of propidium iodide reagent.

(11) DATA ACQUISITION

The flow cytometer is then used to analyze the drug and control samples. Following is an outline of the preferred mode of flow cytometric analysis.

The FSC (forward scatter) and SSC (90-degree or side scatter) settings are placed in linear mode. The FL-1 and FL-2 (fluorescence scales) are placed in logarithmic mode. 5000 acquisition samples are preferred. A negative control tube is placed on the cytometer, a dot-plot is generated, and the FSC and SSC controls are adjusted to position the major cell population(s) in the center of the plot. The negative gate is set in the FL-2 histogram to exclude the negative control population, and this gate is stored for use in the analysis of the drug samples.

If double staining with propidium iodide reagent and CD45-FITC is used due to a non-white cell content of below 80%, additional compensation adjustments must also be made. The CD45-FITC labeled control sample is placed in the flow cytometer and the steps noted above are repeated to produce and store a second negative gate for the CD45 positive subpopulation so that these white cells may later be excluded when analyzing the drug samples.

The data editing function of the flow cytometer is then accessed and each drug sample is analyzed with the control populations excluded. Data is stored for each control and drug sample.

When using the preferred flow cytometer and software, the FACScan running the Consort 30 program, the procedure listed above is performed as follows:

(a) Select CONSORT 30 from the main menu using the mouse.

(b) Insert the data storage disk into the disk drive.

(c) Accept date and time if correct by pressing Y. Settings should be linear on FSC and SSC and logarithmic on FL-1 and FL-2. Adjust as necessary.

(d) Select "acquire and store data" (press 2). The menu will appear.

(e) Select "storage file name" (press 7).

(f) Select "acquisition events" (press 2). Collect 5000 events.

(g) Select "acquire data into memory" (press 5).

(b) Place the control tube on the cytometer, select dot-plot and use the FSC and SSC controls to position the major cell population(s) in the center of the plot. Set FSC threshold as necessary.

NOTE: If double staining with PI and CD45-FITC is used, FL1-FL2 compensation must also be performed by use of the CD45-FITC negative control sample noted above at (10).

(i) Change to FL-2 histogram and use the FL-2 detector control to set the negative gate.

(j) Exit to menu (press 0).

(k) Select "edit text" (press 4).

(l) Enter control sample or drug sample name, patient name, etc. and other such data as desired.

(m) Return to menu (press <cntrl>-0).

(n) Select "acquire and save data" (press <shift>-5) to collect 5000 events.

(o) Repeat steps (k)-(n) until data for all tubes have been collected.

(p) Select "quit program" (press 0) to return to main menu.

(12) DATA ANALYSIS

The flow cytometric analysis software is then used to calculate the percent viability of the positive control and drug samples and compile the viability results of these samples into tabular form. The following steps detail this procedure for the preferred flow cytometer, the FACScan running the Consort 30 program:

(a) Select "read file from disk" (press 3).

(b) Enter file name in correct format starting with tag 1 (control).

(c) Select "read file from disk" (press 2).

(d) Exit (press 0).

(e) Select "analyze data" (press 4).

(f) Select "single histogram" (press 2).

(g) Select "parameter" (<shift>-1 for FL-2).

(h) Select "set markers" (press <shift>-3). Select 2 markers, one at the origin (press ENTER) and the second at the bottom of the negative peak.

(i) Select "display statistics" (press 9) and press "Y" to save data in file.

(j) Obtain hard copy of results (press <shift>-9).

(k) Exit (press 0).

(l) Exit again (press 0) and save the file (enter 14).

(m) Repeat steps (a)-(f) and (i)-(l) until all data have been printed and saved. Do not adjust the markers once they have been set.

The results of the assay are considered to be acceptable if the viability of the positive control sample is less than 50% of the negative control sample(s). If the viability of the positive control sample is greater than 50% of the negative control sample, the results are discarded and a new assay is run.

FORMULATION OF A MULTIDRUG CHEMOTHERAPEUTIC REGIMEN

A multidrug chemotherapeutic regimen is then chosen for the patient based on the results of the pharmacosensitivity assay performed on the patient's tumor. A tumor may be considered to have high sensitivity to a particular drug if greater than 75% of the viable tumor cells are shown to be apoptotic; medium sensitivity if approximately 30–75% of the viable cells are apoptotic; low sensitivity if approximately 15%–30% of the viable tumor cells are apoptotic; and drug resistant if less than 15% of the viable tumor cells are apoptotic. Sensitivity may be rapidly calculated by, for example, custom software or spreadsheet programs.

In general, the multidrug treatment regimen is formulated by selecting the drugs for which the tumor exhibits the highest pharmacosensitivity. Usually, no more than ten drugs are chosen per regimen, with four of these being biological response modifiers (and generally one of these being a hormone). Another preferred treatment is to apply the four or five most effective non-biological response modifier drugs plus one or two biological response modifiers. Treatments wherein four non-biological response modifier drugs plus an alpha interferon (and occasionally an additional biological response modifier, generally a hormone) have been tested with excellent results, some of which are summarized below.

However, it must be remembered that selection criteria based on sensitivity levels will not always formulate the best multidrug treatment regimen. Certain drugs must be eliminated, or dosages must be reduced, if the toxicity of the assay-recommended treatment regimen is too high. Also, the pharmacosensitivity assay results must be interpreted with caution, as the clinical significance of the sensitivity levels has not been established for all drugs in the assay. As examples, levamisole, megestrol acetate, and retinoic acid are not cytotoxic drugs, and tumor cell viability in response to these drugs does not differ significantly from control cells. Therefore, a low level of tumor cell response to these drugs should not be interpreted as drug resistance.

ADMINISTRATION OF THE REGIMEN

The multidrug regimen may be administered by any of the following methods known to the art, such as intravenous administration or even oral administration (where appropriate). The drugs are generally administered at the maximum single-agent dosage recommended by the manufacturer. Dosages are reduced if the combined organ toxicity or the cumulative dosage toxicity of the multidrug regimen is irreversible. Other factors such as the time interval between prior surgery and present chemotherapy and the patient's present status may indicate that lesser dosages should be used.

To insure that the in vivo results of the patient's treatment regimen track the in vitro pharmacosensitivity assay results as closely as possible, the same drug stock is used for both the assay drug samples and the treatment regimen.

One preferred method of drug administration is locoregional administration, in addition to (or in lieu of) systemic administration. Chemotherapy for solid tumors in man is usually given systemically, either orally or intravenously. Consequently, the antitumor effect (the drug level achieved at the target) depends on the blood supply of the solid tumor. Since such blood supply is often small, reducing the delivery of the drug to the tumor, the use of locoregional intra-arterial infusion or perfusion chemotherapy has recently been of interest. Locoregional intra-arterial therapy involves the introduction of a percutaneous (i.e., through the skin) catheter into an artery that feeds the tumor. Chemotherapeutic drugs are then supplied through the catheter, with or without the use of a vasodilator to increase the blood supply to the tumor. As an example, for liver tumors, a catheter would be introduced into the hepatic artery. (Note that while 80%–90% of the blood supply of the liver is derived from the portal vein, the blood supply of liver tumors almost exclusively tends to be from the hepatic artery.) An excellent review of intra-arterial therapy of primary and metasiatic disease may be found in Haskell et al., ed., Cancer Treatment, 3rd. ed., W. B. Saunders Company, 1990.

The theory underlying locoregional intra-arterial drug therapy is that tumor cells should be exposed to higher drug concentrations, and that locoregional administration provides effective delivery of cytotoxic drugs to the tumor in concentrations greater than could be obtained by systemic administration. By supplying the drugs directly to the artery that feeds the tumor, a five- to twenty-fold increase in drug concentration can be obtained in the tumor as compared to systemic therapy, with only minimal toxicity to other organs. Other organs are not exposed to the maximum drug dose because locoregional drug administration achieves high drug concentration only on the "first pass": after the drug passes through the target organ and becomes mixed with the venous blood, any further drug exposure experienced by non-target organs will be the same as though the drug had been given systemically via a peripheral vein. By allowing such dose escalation, marginally effective drugs can be used to increase cell kill, circumvent existing drug resistance mechanisms of the tumor, and prevent the emergence of new drug resistance patterns for the tumor.

However, certain drawbacks to locoregional intra-arterial administration limit its use. It is generally recognized that percutaneously placed angiographic catheters or surgically introduced stiff plastic catheters frequently result in progressive artery thrombosis with decreasing blood flow (or even complete occlusion), catheter displacement, and patient discomfort and inconvenience. Moreover, the often prolonged hospitalization required after percutaneous catheterization is a major obstacle. The catheters are also inconvenient due to the need for frequent maintenance by medical personnel. However, a number of technical developments have largely solved these problems and have greatly improved the feasibility of long-term arterial catheterization and intracavitary treatment.

First, the availability of flexible polymeric silicone (silastic) catheters for surgical placement, e.g., the Hickmann and the Tenckhoff catheter systems, has greatly reduced morbidity, and these systems can remain in place for over a year. For this reason, silastic catheters are preferred.

Second, the problems of maintenance and care have also been reduced by the introduction of portals which can be attached to the intracavitary or intra-arterial catheter and fixed in a subcutaneous pocket to allow repeated access to the peritoneal cavity or the blood vessel in question. As an example, a catheter can be placed in the hepatic artery via the gastroduodenal artery during laparotomy. It can then be threaded through a subcutaneous tunnel and attached to a vascular access port, which also is anchored subcutaneously, usually in the upper anterior rib cage. When a special "HUBER-POINT" (Exel International, Inc., Culver City, Calif., U.S.A.) needle is used, the portal can be punctured through the skin and the thick self-sealing portal septum as often as necessary. Chemotherapeutic agents are then pumped in by a small, external, battery-powered chemoinfusion pump the patient carries in a pouch, achieving continual intra-arterial chemoinfusions. The "PORT-A-CATH" (Harbor Medical Devices, Inc., Jaffrey, N.H., U.S.A.) catheter/portal systems have proven to function admirably well. Of these, the "PORT-A-CATH" is particularly preferred. Its large portal membrane size is of great advantage since the location of a very small subcutaneous membrane via a slippery and sometimes fluid-filled pocket may be troublesome, particularly in obese patients.

For outpatients, continuous drug infusion can be provided by a totally implantable subcutaneous pump, e.g. the "INFUSAID" pump (Infusaid Corp., Norwood, Mass.). The "INFUSAID" utilizes an expandable reservoir inside a smooth, rigid titanium external shell. Between the shell and the reservoir is a fluorocarbon liquid in equilibrium with its vapor phase, and a catheter is attached to the reservoir. During laparotomy, the pump is placed in a subcutaneous pocket, and the catheter is inserted into the hepatic artery. The reservoir, which holds 50 ml, is filled through a silastic port in the pump by insertion of a needle through the skin and subcutaneous tissue. The pressure of this injection expands the bellowslike reservoir, simultaneously filling the pump and condensing the fluorocarbon. Since at 37° C. the vapor pressure of the substance is 300 mm greater than atmospheric pressure, the heat of the body causes a phase change in the fluorocarbon, and the expanding vapor exerts force on the bellows, which forces the infusate through a flow-regulating resistance element and out the catheter. At flow rates of 2 to 3 ml per 24 hours, the pump can run for 14 to 21 days without refilling. Each refilling recharges the driving mechanism. The device is quiet and efficient and has proved to be virtually free of mechanical or technical problems.

There are several significant advantages to totally implantable subcutaneous pumps. Patient acceptance has been enthusiastic since all forms of activity, including recreational activities such as tennis, swimming, and golf, are unimpaired. Filling the pump has proved to be a relatively quick and painless procedure, and the scarification of veins common with intravenous administration of therapeutic agents is obviated. Most important, because the entire system is internalized and because of the unique thick-walled, small-diameter lumen design of the catheter of the "INFUSAID" system, catheter occlusion and migration have been virtually unknown. With these technical improvements, long-term periods of continuous infusion can be accomplished. This technology has largely eliminated the vagaries of external catheter occlusions, displacement, inadvertent withdrawal, and similar technical problems that have plagued hepatic artery infusion chemotherapy in the past.

Another alternative is an extracorporeal pumping device such as the "ACT-A-PUMP" (Pharmacia, Dublin, Ohio, U.S.A.). Extracorporeal pumps are economical since they may be used for more than one patient, but they tend to be more inconvenient to the patient because the patient requires a continuous percutaneous needle connection to an external pump.

The procedure of the invention has achieved exceptionally favorable results in the treatment of metastatic tumors, particularly metastatic liver tumors, by use of locoregional infusion. Generally, metastatic tumors are treated with the same regimen used for treating a primary tumor. As numerous studies in the art illustrate, this often results in the defeat of the primary tumor only to have the metastases overwhelm the patient; a battle is won, but the war is lost. It has been found that where the drug treatment regimen of the procedure is developed by pharmacosensitivity testing of a metastatic tumor sample, the regimen is highly effective not only on the metastases, but on the primary tumor as well. The metastases are treated by locoregional infusion, while the primary tumor may be treated simultaneously by systemic administration (or can also be treated locoregionally, if appropriate). When the primary tumor is no longer present, the locoregional treatment of the metastases may be continued; alternatively, if the metastases are eliminated, the systemic treatment of the primary tumor may continue. The results of treatment by simultaneous locoregional and systemic administration of chemotherapy dictated by testing of metastases are given in Experiments 29–33 below. The classical oncologist might view the treatment applied in these experiments to be an aggressive approach, but it is believed that any inconveniences presented by the use of locoregional therapy are outweighed by the fact that the procedure offers far better response rates than prior art treatments.

The three methods of locoregional intra-arterial administration used most often in the procedure have been:

(1) Super-selective catheterization wherein the catheter is inserted in the tumor nutrition artery. Generally, drugs are injected one to three times a day for 3 to 7 days.

(2) The catheter is placed in the tumor nutrition artery, generally once per week, and after drugs are administered it is removed. This procedure is repeated, generally until remission.

(3) A permanent catheter is surgically implanted and the drugs are administered by continuous infusion. All three methods have met with positive results with minimal ill effects in the patient.

Before the catheter is installed, the patient's vascular system should be carefully examined because insufficient knowledge about vascular anomalies can result in non-optimal infusion of the target organ. Ligation of vessels and the use of more than one catheter may be necessary to obtain optimal infusion of the organ.

It must be remembered that while many drugs can be applied either systemically or locoregionally, not all drugs are appropriate for all types of administration. As one example, mechlorethamine hydrochloride (nitrogen mustard) is too toxic to veins to be applied locoregionally. As another example, many of the drugs would either be ineffective or deadly if applied orally. The manufacturer's instructions for use should be carefully followed in every case. Additionally, if locoregional and systemic administration are used simultaneously, dosages must be adjusted to account for overall toxicity. When the dosages of the systemically-applied drugs are adjusted to account for the locoregionally-administered dosages, simultaneous locoregional and systemic treatment is actually much less toxic than general systemic therapy alone. In some cases, depending on the drug take-up of the target organ, it may be possible to forego systemic administration in lieu of locoregional administration because the venous blood exiting the target organ may carry the dosages appropriate for systemic therapy.

EXPERIMENTAL RESULTS

Following is a summary of experimental results obtained by use of the procedure described above. Experiments 1–28 were performed to determine the variation in drug sensitivity between patient tumors as determined by the pharmacosensitivity assay of the procedure, and these experiments demonstrated that the same and similar types of tumors vary widely in in vitro response to the same drugs from patient to patient. Experiments 29–33 tested the efficacy of the treatment procedure on candidates with primary liver tumors and liver metastases, wherein the drugs were administered intra-arterially to the liver via the hepatic artery.

Experiment 1: Patient (1) suffered from pancreatic cancer. A tumor sample was tested by the preferred embodiment of the pharmacosensitivity assay as set out above and the following results were obtained:

| High Sensitivity | |
| --- | --- |
| Fludarabine phosphate | 94.3% |
| Doxorubicin | 93.1% |
| Dactinomycin | 92.8% |
| Taxol | 84.8% |
| Intermediate Sensitivity | |
| Etoposide | 71.9% |
| Mito-C | 68.1% |
| Thio-TEPA | 52.1% |
| nHuIFNπ | 49.5% |
| VBL | 37.3% |
| Ifosfamide/Mesna | 35.5% |
| Low Sensitivity | |
| 5-FU | 31.7% |
| Bleomycin | 31.1% |
| nHuIFNα | 30.6% |
| rIFNβ-1b | 28.3% |
| Cyclophosphamide | 27.4% |
| rIFNτ-1b | 26.7% |
| Prednisone | 26.5% |
| GM-CSF | 25.7% |
| Ifosfamide | 22.7% |
| VCR | 22.3% |
| Resistant | |
| Paraplatin | 19.7% |
| rIFNα-2a | 13.2% |
| Floxuridine | 12.9% |
| nHuIFNβ | 12.4% |
| rIL-2 | 8.8% |
| Cisplatin | 8.7% |
| rTNF | 7.5% |
| Amethopterin | 6.4% |
| Retinoic acid | 3.5% |
| G-CSF | 3.4% |
| Hydrea | 2.9% |
| Megestrol Acetate | 2.1% |
| Tamoxifen | 0.0% |

The positive (Abrin) control sample demonstrated 99.6% cell kill as compared to the negative control sample.

Experiment 2: Patient (2) suffered from pancreatic cancer. A tumor sample was tested by the preferred embodiment of the pharmacosensitivity assay as set out above and the following results were obtained:

| High Sensitivity | |
|---|---|
| Dactinomycin | 99.5% |
| Doxorubicin | 98.0% |
| Tamoxifen | 94.6% |
| Mito-C | 92.1% |
| 5-FU | 89.8% |
| Intermediate Sensitivity | |
| Taxol | 77.6% |
| Retinoic acid | 64.8% |
| Etoposide | 54.0% |
| G-CSF | 51.7% |
| Amethopterin | 50.2% |
| Ifosfamide | 47.5% |
| Floxuridine | 44.7% |
| rTNF | 43.5% |
| rIFNα-2a | 40.5% |
| Low Sensitivity | |
| Ifosfamide/Mesna | 34.3% |
| rIFNβ-1b | 34.2% |
| GM-CSF | 32.3% |
| rIFNβ-1b | 29.1% |
| rIFNτ-1b | 28.2% |
| Medroxyprogesterone | 25.6% |
| BCNU | 25.1% |
| Megestrol Acetate | 23.4% |
| rIL-2 | 21.2% |
| Streptozocin | 21.2% |
| Resistant | |
| VCR | 19.3% |
| VBL | 9.6% |
| Somatostatin | 0.0% |
| nHuIFNα | 0.0% |
| nHuIFNπ | 0.0% |

The positive (Abrin) control sample demonstrated 99.7% cell kill as compared to the negative control sample.

Experiment 3: Patient (3) suffered from pancreatic cancer. A tumor sample was tested by the preferred embodiment of the pharmacosensitivity assay as set out above and the following results were obtained:

| Intermediate Sensitivity | |
|---|---|
| G-CSF | 53.5% |
| GM-CSF | 53.5% |
| rIFNτ-1b | 50.1% |
| Doxorubicin | 43.9% |
| Mito-C | 43.9% |
| rTNF | 41.1% |
| nHuIFNβ | 38.7% |
| Low Sensitivity | |
| nHuIFNπ | 29.4% |
| Dactinomycin | 27.3% |
| rIFNβ-1b | 23.0% |
| VBL | 22.3% |
| VCR | 21.6% |
| Resistant | |
| Ifosfamide/Mesna | 18.1% |
| rIL-2 | 17.7% |
| Ifosfamide | 12.7% |
| BCNU | 11.5% |
| Retinoic acid | 11.1% |
| 5-FU | 10.9% |
| Amethopterin | 9.7% |
| Etoposide | 0.0% |
| Floxuridine | 0.0% |
| Streptozocin | 0.0% |
| Taxol | 0.0% |
| Megestrol Acetate | 0.0% |
| Medroxyprogesterone | 0.0% |
| Somatostatin | 0.0% |
| Tamoxifen | 0.0% |
| nHuIFNα | 0.0% |
| rIFNα-2a | 0.0% |

The positive (Abrin) control sample demonstrated 66.5% cell kill as compared to the negative control sample.

Experiment 4: Patient (4) suffered from pancreatic cancer. A tumor sample was tested by the preferred embodiment of the pharmacosensitivity assay as set out above and the following results were obtained:

| High Sensitivity | |
|---|---|
| Dactinomycin | 86.9% |
| Doxorubicin | 83.9% |
| Intermediate Sensitivity | |
| Medroxyprogesterone | 71.0% |
| rIFNα-2a | 48.7% |
| Mito-C | 48.2% |
| G-CSF | 47.1% |
| nHuIFNπ | 46.9% |
| GM-CSF | 41.3% |
| Megestrol Acetate | 39.8% |
| rIFNβ-1b | 38.3% |
| Low Sensitivity | |
| rTNF | 33.5% |
| Tamoxifen | 32.2% |
| 5-FU | 31.7% |
| nHuIFNβ | 30.6% |
| rIFNτ-1b | 24.4% |
| VCR | 21.3% |
| Retinoic acid | 20.3% |
| Resistant | |
| Floxuridine | 8.0% |
| VBL | 7.6% |
| BCNU | 4.6% |
| Streptozocin | 3.2% |
| Ifosfamide/Mesna | 1.3% |
| Amethopterin | 0.2% |
| Etoposide | 0.0% |
| Ifosfamide | 0.0% |
| Taxol | 0.0% |
| Somatostatin | 0.0% |
| nHuIFNα | 0.0% |
| rIL-2 | 0.0% |

The positive (Abrin) control sample demonstrated 31.7% cell kill as compared to the negative control sample.

Experiment 5: Patient (5) suffered from pancreatic cancer. A tumor sample was tested by the preferred embodiment of the pharmacosensitivity assay as set out above and the following results were obtained:

| High Sensitivity | |
|---|---|
| Doxorubicin | 98.5% |
| Dactinomycin | 95.6% |
| Intermediate Sensitivity | |
| Mito-C | 73.8% |
| VBL | 39.1% |
| VCR | 35.3% |
| Low Sensitivity | |
| BCNU | 23.5% |

| Resistant | |
|---|---|
| Retinoic acid | 17.8% |
| 5-FU | 15.2% |
| Tamoxifen | 14.8% |
| Streptozocin | 12.8% |
| Medroxyprogesterone | 11.6% |
| Somatostatin | 7.8% |
| Ifosfamide/Mesna | 7.7% |
| rIL-2 | 5.5% |
| nHuIFNα | 2.7% |
| Floxuridine | 2.5% |
| Taxol | 0.7% |
| Etoposide | 0.0% |
| Ifosfamide | 0.0% |
| Amethopterin | 0.0% |
| G-CSF | 0.0% |
| GM-CSF | 0.0% |
| Megestrol Acetate | 0.0% |
| nHuIFNβ | 0.0% |
| nHuIFNπ | 0.0% |
| rIFNα-2a | 0.0% |
| rIFNβ-1b | 0.0% |
| rIFNτ-1b | 0.0% |
| rTNF | 0.0% |

The positive (Abrin) control sample demonstrated 88.1% cell kill as compared to the negative control sample.

Experiment 6: Patient (6) suffered from pancreatic cancer. A tumor sample was tested by the preferred embodiment of the pharmacosensitivity assay as set out above and the following results were obtained:

| High Sensitivity | |
|---|---|
| Doxorubicin | 99.8% |
| Medroxyprogesterone | 96.0% |
| Dactinomycin | 94.7% |
| Tamoxifen | 86.3% |
| Mito-C | 81.5% |
| Intermediate Sensitivity | |
| Taxol | 77.2% |
| Etoposide | 67.4% |
| BCNU | 61.9% |
| rIFNτ-1b | 48.0% |
| VBL | 47.5% |
| nHuIFNα | 46.8% |
| Megestrol Acetate | 46.6% |
| rTNF | 45.7% |
| VCR | 45.4% |
| G-CSF | 45.4% |
| GM-CSF | 44.6% |
| nHuIFNβ | 39.1% |
| Low Sensitivity | |
| nHuIFNπ | 34.9% |
| 5-FU | 25.0% |
| Resistant | |
| rIL-2 | 17.0% |
| Ifosfamide | 7.4% |
| Streptozocin | 5.4% |
| rIFNβ-1b | 2.8% |
| Amethopterin | 1.3% |
| Floxuridine | 0.0% |
| Ifosfamide/Mesna | 0.0% |
| Somatostatin | 0.0% |
| rIFNα-2a | 0.0% |

The positive (Abrin) control sample demonstrated 98.7% cell kill as compared to the negative control sample.

Experiment 7: Patient (7) suffered from acute myelogenous leukemia. A tumor sample was tested by the preferred embodiment of the pharmacosensitivity assay as set out above and the following results were obtained:

| High Sensitivity | |
|---|---|
| Doxorubicin | 99.7% |
| Ara-C | 95.3% |
| Fludarabine phosphate | 80.3% |
| Intermediate Sensitivity | |
| GM-CSF | 77.6% |
| G-CSF | 56.5% |
| nHuIFNπ | 49.7% |
| Cyclophosphamide | 45.2% |
| nHuIFNα | 44.6% |
| Prednisone | 44.0% |
| Hydrea | 43.9% |
| rIFNτ-1b | 43.6% |
| rTNF | 41.5% |
| nHuIFNβ | 38.7% |
| Resistant | |
| rIFNβ-1b | 16.3% |
| Amethopterin | 13.6% |
| rIFNα-2a | 10.8% |
| Cladribine | 0.0% |
| rIL-2 | 0.0% |

The positive (Abrin) control sample demonstrated 98.8% cell kill as compared to the negative control sample.

Experiment 8: Patient (8) suffered from breast cancer. A tumor sample was tested by the preferred embodiment of the pharmacosensitivity assay as set out above and the following results were obtained:

| Intermediate Sensitivity | |
|---|---|
| Taxol | 68.3% |
| nHuIFNβ | 62.1% |
| nHuIFNπ | 61.7% |
| GM-CSF | 60.2% |
| Doxorubicin | 56.5% |
| rIFNτ-1b | 55.7% |
| rTNF | 55.1% |
| Ara-C | 48.7% |
| nHuIFNα | 48.1% |
| G-CSF | 44.4% |
| Medroxyprogesterone | 43.1% |
| Melphalan | 41.9% |
| Etoposide | 36.6% |
| Low Sensitivity | |
| Ifosfamide | 33.7% |
| Ifosfamide/Mesna | 31.4% |
| Thio-TEPA | 29.4% |
| rIFNα-2a | 24.4% |
| Mito-C | 22.6% |
| VBL | 22.1% |
| Resistant | |
| VCR | 19.4% |
| Prednisone | 17.3% |
| rIFNβ-1b | 17.0% |
| Tamoxifen | 15.8% |
| Hydrea | 12.2% |
| Cisplatin | 11.0% |
| 5-FU | 8.3% |
| Cyclophosphamide | 7.3% |
| Amethopterin | 5.1% |
| Paraplatin | 3.8% |
| rIL-2 | 3.2% |
| Floxuridine | 0.0% |
| DTIC | 0.0% |
| Somatostatin | 0.0% |

The positive (Abrin) control sample demonstrated 99.7% cell kill as compared to the negative control sample.

Experiment 9: Patient (9) suffered from breast cancer with liver metastases. A tumor sample was tested by the preferred embodiment of the pharmacosensitivity assay as set out above and the following results were obtained:

| High Sensitivity | |
| --- | --- |
| Taxol | 93.5% |
| rTNF | 90.5% |
| rIFNτ-1b | 89.7% |
| nHuIFNα | 85.0% |
| nHuIFNβ | 81.7% |
| nHuIFNπ | 80.4% |
| Intermediate Sensitivity | |
| G-CSF | 78.3% |
| GM-CSF | 77.2% |
| Doxorubicin | 46.1% |
| Resistant | |
| Tamoxifen | 13.1% |
| Etoposide | 12.2% |
| BCNU | 7.6% |
| Megestrol Acetate | 3.6% |
| Medroxyprogesterone | 2.4% |
| Ara-C | 2.0% |
| Prednisone | 1.5% |
| MITO-C | 0.9% |
| 5-FU | 0.7% |
| Ifosfamide-Mesna | 0.6% |
| VBL | 0.3% |
| Paraplatin | 0.0% |
| Cisplatin | 0.0% |
| Cyclophosphamide | 0.0% |
| Floxuridine | 0.0% |
| Ifosfamide | 0.0% |
| Amethopterin | 0.0% |
| VCR | 0.0% |
| Somatostatin | 0.0% |
| rIL-2 | 0.0% |
| rIFNα-2a | 0.0% |
| rIFNβ-1b | 0.0% |

The positive (Abrin) control sample demonstrated 75.0% cell kill as compared to the negative control sample.

Experiment 10: Patient (10) suffered from breast cancer. A tumor sample was tested by the preferred embodiment of the pharmacosensitivity assay as set out above and the following results were obtained:

| High Sensitivity | |
| --- | --- |
| Doxorubicin | 93.7% |
| Intermediate Sensitivity | |
| VCR | 57.9% |
| Megestrol Acetate | 54.4% |
| Somatostatin | 54.4% |
| Tamoxifen | 51.6% |
| Cyclophosphamide | 49.0% |
| Floxuridine | 47.1% |
| Etoposide | 44.0% |
| Ifosfamide/Mesna | 42.1% |
| BCNU | 42.0% |
| nHuIFNπ | 40.5% |
| Low Sensitivity | |
| Cisplatin | 39.9% |
| Prednisone | 37.0% |
| Ifosfamide | 35.1% |
| VBL | 33.9% |
| 5-FU | 29.2% |
| Paraplatin | 25.6% |
| Taxol | 21.5% |
| Resistant | |
| Ara-C | 19.3% |
| Amethopterin | 18.7% |
| Mito-C | 18.1% |
| rIFNα-2a | 18.0% |
| rIFNβ-1b | 17.5% |
| rTNF | 3.5% |
| G-CSF | 0.0% |
| GM-CSF | 0.0% |
| Medroxyprogesterone | 0.0% |
| nHuIFNα | 0.0% |
| nHuIFNβ | 0.0% |
| rIFNτ-1b | 0.0% |

The positive (Abrin) control sample demonstrated 52.8% cell kill as compared to the negative control sample.

Experiment 11: Patient (11) suffered from bladder cancer. A tumor sample was tested by the preferred embodiment of the pharmacosensitivity assay as set out above and the following results were obtained:

| Intermediate Sensitivity | |
| --- | --- |
| Bleomycin | 77.3% |
| rIFNα-2a | 69.2% |
| rIFNτ-1b | 61.1% |
| Mito-C | 58.3% |
| rIFNβ-1b | 43.1% |
| Hydrea | 42.2% |
| Low Sensitivity | |
| Retinoic acid | 34.6% |
| Floxuridine | 29.4% |
| Amethopterin | 24.2% |

The positive (Abrin) control sample demonstrated 97.6% cell kill as compared to the negative control sample.

Experiment 12: Patient (12) suffered from bladder cancer. A tumor sample was tested by the preferred embodiment of the pharmacosensitivity assay as set out above and the following results were obtained:

| Intermediate Sensitivity | |
| --- | --- |
| Bleomycin | 77.3% |
| rIFNα-2a | 69.2% |
| rIFNτ-1b | 61.1% |
| Mito-C | 58.3% |
| rIFNβ-1b | 43.1% |
| Hydrea | 42.2% |
| Low Sensitivity | |
| Retinoic acid | 34.6% |
| Floxuridine | 29.4% |
| Amethopterin | 24.2% |

The positive (Abrin) control sample demonstrated 97.6% cell kill as compared to the negative control sample.

Experiment 13: Patient (13) suffered from chronic myelogenous leukemia. A tumor sample was tested by the preferred embodiment of the pharmacosensitivity assay as set out above and the following results were obtained:

| High Sensitivity | |
| --- | --- |
| Doxorubicin | 94.0% |
| Fludarabine phosphate | 81.0% |
| Ara-C | 80.6% |

-continued

| Intermediate Sensitivity | |
|---|---|
| Hydrea | 50.1% |
| Cyclophosphamide | 38.9% |
| Resistant | |
| nHuIFNβ | 19.1% |
| nHuIFNπ | 15.1% |
| rTNF | 13.5% |
| Amethopterin | 12.2% |
| Prednisone | 9.0% |
| rIFNτ-1b | 8.9% |
| rIFNβ-1b | 8.3% |
| rIFNα-2a | 7.9% |
| G-CSF | 0.0% |
| GM-CSF | 0.0% |
| Somatostatin | 0.0% |
| nHuIFNα | 0.0% |
| rIL-2 | 0.0% |

The positive (Abrin) control sample demonstrated 99.6% cell kill as compared to the negative control sample.

Experiment 14: Patient (14) suffered from chronic myelogenous leukemia. A tumor sample was tested by the preferred embodiment of the pharmacosensitivity assay as set out above and the following results were obtained:

| Intermediate Sensitivity | |
|---|---|
| Fludarabine phosphate | 65.1% |
| Ara-C | 60.1% |
| Cladribine | 58.3% |
| rIFNβ-1b | 49.2% |
| Doxorubicin | 42.9% |
| nHuIFNβ | 40.3% |
| Low Sensitivity | |
| Hydrea | 32.7% |
| rIFNα-2a | 30.3% |
| Prednisone | 27.8% |
| Amethopterin | 26.9% |
| nHuIFNπ | 24.9% |
| Cyclophosphamide | 23.3% |
| rIFNτ-1b | 23.0% |
| Resistant | |
| nHuIFNα | 18.3% |
| rTNF | 14.1% |
| rIL-2 | 13.9% |
| Etoposide | 11.1% |
| Somatostatin | 8.1% |
| G-CSF | 0.0% |
| GM-CSF | 0.0% |

The positive (Abrin) control sample demonstrated 99.6% cell kill as compared to the negative control sample.

Experiment 15: Patient (15) suffered from chronic myelogenous leukemia. A tumor sample was tested by the preferred embodiment of the pharmacosensitivity assay as set out above and the following results were obtained:

| High Sensitivity | |
|---|---|
| Doxorubicin | 99.9% |
| Intermediate Sensitivity | |
| G-CSF | 60.4% |
| Hydrea | 52.0% |
| Ara-C | 47.1% |
| Fludarabine phosphate | 46.3% |
| Cladribine | 44.3% |
| GM-CSF | 41.7% |
| rIFNβ-1b | 40.2% |
| nHuIFNπ | 35.4% |
| Low Sensitivity | |
| nHuIFNβ | 27.3% |
| nHuIFNα | 25.8% |
| rTNF | 24.0% |
| rIFNα-2a | 23.7% |
| Resistant | |
| rIFNτ-1b | 20.0% |
| Amethopterin | 10.5% |
| Cyclophosphamide | 3.8% |
| Prednisone | 2.2% |
| Somatostatin | 0.0% |
| rIL-2 | 0.0% |

The positive (Abrin) control sample demonstrated 99.7% cell kill as compared to the negative control sample.

Experiment 16: Patient (16) suffered from chronic myelogenous leukemia. A tumor sample was tested by the preferred embodiment of the pharmacosensitivity assay as set out above and the following results were obtained:

| High Sensitivity | |
|---|---|
| Doxorubicin | 94.0% |
| Fludarabine phosphate | 81.0% |
| Ara-C | 80.6% |
| Intermediate Sensitivity | |
| Hydrea | 50.1% |
| Cyclophosphamide | 38.9% |
| Resistant | |
| nHuIFNβ | 19.1% |
| nHuIFNπ | 15.1% |
| rTNF | 13.5% |
| Amethopterin | 12.2% |
| Prednisone | 9.0% |
| rIFNτ-1b | 8.9% |
| rIFNβ-1b | 8.3% |
| rIFNα-2a | 7.9% |
| G-CSF | 0.0% |
| GM-CSF | 0.0% |
| Somatostatin | 0.0% |
| nHuIFNα | 0.0% |
| rIL-2 | 0.0% |

The positive (Abrin) control sample demonstrated 99.6% cell kill as compared to the negative control sample.

Experiment 17: Patient (17) suffered from chronic myelogenous leukemia. A tumor sample was tested by the preferred embodiment of the pharmacosensitivity assay as set out above and the following results were obtained:

| High Sensitivity | |
|---|---|
| Doxorubicin | 99.8% |
| Fludarabine phosphate | 98.8% |
| Ara-C | 98.2% |
| Prednisone | 82.2% |
| Intermediate Sensitivity | |
| Cyclophosphamide | 53.6% |
| Hydrea | 45.7% |
| rIFNα-2a | 43.4% |
| rIFNτ-1b | 42.3% |
| nHuIFNβ | 39.5% |
| nHuIFNπ | 39.3% |

39
-continued

| | |
|---|---|
| rIFNβ-1b | 35.6% |
| Low Sensitivity | |
| | |
| nHuIFNα | 33.3% |
| rTNF | 25.6% |
| G-CSF | 21.0% |
| Resistant | |
| | |
| Amethopterin | 15.2% |
| Somatostatin | 14.1% |
| rIL-2 | 5.5% |
| GM-CSF | 0.0% |

The positive (Abrin) control sample demonstrated 97.9% cell kill as compared to the negative control sample.

Experiment 18: Patient (18) suffered from chronic myelogenous leukemia. A tumor sample was tested by the preferred embodiment of the pharmacosensitivity assay as set out above and the following results were obtained:

| High Sensitivity | |
|---|---|
| Doxorubicin | 98.5% |
| Intermediate Sensitivity | |
| | |
| rTNF | 66.8% |
| G-CSF | 54.3% |
| Fludarabine phosphate | 52.0% |
| nHuIFNπ | 49.3% |
| Ara-C | 46.7% |
| nHuIFNα | 43.8% |
| rIFNτ-1b | 43.6% |
| GM-CSF | 39.7% |
| nHuIFNβ | 36.8% |
| Cyclophosphamide | 35.9% |
| Low Sensitivity | |
| | |
| Prednisone | 31.1% |
| Resistant | |
| | |
| Hydrea | 0.0% |
| Amethopterin | 0.0% |
| Somatostatin | 0.0% |
| rIL-2 | 0.0% |
| rIFNα-2a | 0.0% |
| rIFNβ-1b | 0.0% |

The positive (Abrin) control sample demonstrated 97.9% cell kill as compared to the negative control sample.

Experiment 19: Patient (19) suffered from chronic myelogenous leukemia. A tumor sample was tested by the preferred embodiment of the pharmacosensitivity assay as set out above and the following results were obtained:

| High Sensitivity | |
|---|---|
| Doxorubicin | 99.1% |
| Intermediate Sensitivity | |
| | |
| Ara-C | 69.8% |
| Fludarabine phosphate | 59.5% |
| Low Sensitivity | |
| | |
| nHuIFNπ | 34.7% |
| nHuIFNβ | 28.9% |
| nHuIFNα | 26.7% |
| Hydrea | 26.6% |
| G-CSF | 25.0% |
| Resistant | |
| | |
| Cyclophosphamide | 18.2% |

40
-continued

| | |
|---|---|
| rTNF | 16.8% |
| rIFNτ-1b | 16.4% |
| GM-CSF | 14.5% |
| Prednisone | 12.7% |
| rIFNβ-1b | 5.8% |
| Amethopterin | 2.3% |
| Somatostatin | 0.0% |
| rIL-2 | 0.0% |
| rIFNα-2a | 0.0% |

The positive (Abrin) control sample demonstrated 99.4% cell kill as compared to the negative control sample.

Experiment 20: Patient (20) suffered from Waldenstrom's macroglobulinemia. A tumor sample was tested by the preferred embodiment of the pharmacosensitivity assay as set out above and the following results were obtained:

| High Sensitivity | |
|---|---|
| rIFNτ-1b | 91.8% |
| Intermediate Sensitivity | |
| | |
| nHuIFNπ | 58.4% |
| rTNF | 48.2% |
| G-CSF | 46.7% |
| nHuIFNβ | 42.1% |
| Fludarabine phosphate | 36.4% |
| nHuIFNα | 35.6% |
| Low Sensitivity | |
| | |
| GM-CSF | 33.7% |
| Etoposide | 31.6% |
| Medroxyprogesterone | 30.9% |
| Ara-C | 27.4% |
| rIFNα-2a | 25.9% |
| Melphalan | 23.2% |
| rIFNβ-1b | 21.0% |
| Resistant | |
| | |
| Cladribine | 17.2% |
| 5-FLUOROURACIL | 16.6% |
| Ifosfamide | 14.8% |
| Cyclophosphamide | 14.6% |
| Tamoxifen | 11.2% |
| VCR | 8.4% |
| Ifosfamide/Mesna | 7.6% |
| VBL | 5.2% |
| Doxorubicin | 3.7% |
| Somatostatin | 0.5% |
| Cisplatin | 0.0% |
| rIL-2 | 0.0% |

The positive (Abrin) control sample demonstrated 98.5% cell kill as compared to the negative control sample.

Experiment 21: Patient (21) suffered from Waldenstrom's macroglobulinemia. A tumor sample was tested by the preferred embodiment of the pharmacosensitivity assay as set out above and the following results were obtained:

| Intermediate Sensitivity | |
|---|---|
| Doxorubicin | 60.5% |
| Ara-C | 35.6% |
| Low Sensitivity | |
| | |
| Fludarabine phosphate | 30.2% |
| Mito-C | 23.9% |
| Ifosfamide/Mesna | 21.6% |
| Resistant | |
| | |
| rIFNβ-1b | 10.1% |

| | |
|---|---|
| rIFNα-2a | 8.8% |
| nHuIFNπ | 4.1% |
| nHuIFNβ | 3.5% |
| nHuIFNα | 3.3% |
| Cyclophosphamide | 1.7% |
| Cisplatin | 0.0% |
| Etoposide | 0.0% |
| 5-FU | 0.0% |
| Melphalan | 0.0% |
| VBL | 0.0% |
| VCR | 0.0% |
| G-CSF | 0.0% |
| GM-CSF | 0.0% |
| Medroxyprogesterone | 0.0% |
| Somatostatin | 0.0% |
| Tamoxifen | 0.0% |
| rIL-2 | 0.0% |
| rIFNτ-1b | 0.0% |
| rTNF | 0.0% |

The positive (Abrin) control sample demonstrated 91.6% cell kill as compared to the negative control sample.

Experiment 22: Patient (22) suffered from Waldenstrom's macroglobulinemia. A tumor sample was tested by the preferred embodiment of the pharmacosensitivity assay as set out above and the following results were obtained:

| High Sensitivity | |
|---|---|
| Doxorubicin | 98.1% |
| Intermediate Sensitivity | |
| Fludarabine phosphate | 50.4% |
| Ara-C | 41.7% |
| Medroxyprogesterone | 39.3% |
| Low Sensitivity | |
| Mito-C | 22.5% |
| Ifosfamide/Mesna | 20.1% |
| Resistant | |
| Cyclophosphamide | 15.3% |
| VBL | 9.4% |
| Tamoxifen | 6.2% |
| Ifosfamide | 3.1% |
| Cisplatin | 2.8% |
| rIL-2 | 2.2% |
| nHuIFNα | 1.1% |
| Etoposide | 0.0% |
| 5-FU | 0.0% |
| Melphalan | 0.0% |
| VCR | 0.0% |
| G-CSF | 0.0% |
| GM-CSF | 0.0% |
| Somatostatin | 0.0% |
| nHuIFNβ | 0.0% |
| nHuIFNπ | 0.0% |
| rIFNα-2a | 0.0% |
| rIFNβ-1b | 0.0% |
| rIFNτ-1b | 0.0% |
| rTNF | 0.0% |

The positive (Abrin) control sample demonstrated 99.0% cell kill as compared to the negative control sample.

Experiment 23: Patient (23) suffered from non-Hodgkin's lymphoma. A tumor sample was tested by the preferred embodiment of the pharmacosensitivity assay as set out above and the following results were obtained:

| Intermediate Sensitivity | |
|---|---|
| Fludarabine phosphate | 36.4% |
| Low Sensitivity | |
| rTNF | 21.1% |
| Ifosfamide | 21.0% |
| Resistant | |
| Etoposide | 20.0% |
| Doxorubicin | 11.1% |
| Cyclophosphamide | 10.0% |
| nHuIFNπ | 8.9% |
| BCNU | 7.7% |
| rIFNτ-1b | 5.4% |
| VBL | 5.2% |
| Ifosfamide/Mesna | 5.1% |
| rIFNβ-1b | 3.0% |
| Mechlorethamine hydrochloride | 1.0% |
| nHuIFNβ | 0.3% |
| Bleomycin | 0.0% |
| DTIC | 0.0% |
| Hydrea | 0.0% |
| Amethopterin | 0.0% |
| Streptozocin | 0.0% |
| VCR | 0.0% |
| Somatostatin | 0.0% |
| nHuIFNα | 0.0% |
| rIFNα-2a | 0.0% |
| rIL-3 | 0.0% |
| rIL-2 | 0.0% |

The positive (Abrin) control sample demonstrated 96.8% cell kill as compared to the negative control sample.

Experiment 24: Patient (24) suffered from osteogenic sarcoma. A tumor sample was tested by the preferred embodiment of the pharmacosensitivity assay as set out above and the following results were obtained:

| High Sensitivity | |
|---|---|
| Doxorubicin | 99.8% |
| Ara-C | 97/7% |
| Intermediate Sensitivity | |
| Mito-C | 59.6% |
| rIFNβ-1b | 44.6% |
| Resistant | |
| 5-FU | 20.0% |
| Cisplatin | 17.0% |
| Etoposide | 16.6% |
| nHuIFNπ | 12.5% |
| rIL-2 | 9.9% |
| DTIC | 8.4% |
| Floxuridine | 5.7% |
| nHuIFNβ | 5.4% |
| Amethopterin | 3.3% |
| Bleomycin | 0.0% |
| Cyclophosphamide | 0.0% |
| Ifosfamide | 0.0% |
| Ifosfamide/Mesna | 0.0% |
| Melphalan | 0.0% |
| VBL | 0.0% |
| VCR | 0.0% |
| G-CSF | 0.0% |
| GM-CSF | 0.0% |
| Somatostatin | 0.0% |
| nHuIFNα | 0.0% |
| rIFNα-2a | 0.0% |
| rIFNτ-1b | 0.0% |
| rTNF | 0.0% |

The positive (Abrin) control sample demonstrated 99.6% cell kill as compared to the negative control sample.

Experiment 25: Patient (25) suffered from ovarian carcinoma. A tumor sample was tested by the preferred embodiment of the pharmacosensitivity assay as set out above and the following results were obtained:

| | |
|---|---|
| High Sensitivity | |
| Doxorubicin | 86.7% |
| Intermediate Sensitivity | |
| Ifosfamide | 74.9% |
| rIFNβ-1b | 72.5% |
| G-CSF | 68.2% |
| GM-CSF | 66.8% |
| Ara-C | 66.4% |
| rIFNτ-1b | 63.5% |
| rTNF | 62.6% |
| Taxol | 62.1% |
| nHuIFNα | 60.7% |
| nHuIFNπ | 60.2% |
| Mito-C | 55.5% |
| 5-FU | 51.7% |
| Floxuridine | 46.4% |
| VBL | 43.6% |
| VCR | 44.1% |
| Tamoxifen | 41.7% |
| Megestrol Acetate | 40.8% |
| Somatostatin | 40.8% |
| Cyclophosphamide | 39.8% |
| Amethopterin | 39.3% |
| Low Sensitivity | |
| rIFNα-2a | 34.1% |
| Resistant | |
| DTIC | 14.2% |
| nHuIFNβ | 7.6% |
| BCNU | 0.0% |
| Cisplatin | 0.0% |
| Etoposide | 0.0% |
| Medroxyprogesterone | 0.0% |
| rIL-2 | 0.0% |

The positive (Abrin) control sample demonstrated 78.7% cell kill as compared to the negative control sample.

Experiment 26: Patient (26) suffered from glioblastima multiforma. A tumor sample was tested by the preferred embodiment of the pharmacosensitivity assay as set out above and the following results were obtained:

| | |
|---|---|
| High Sensitivity | |
| nHuIFNβ | 95.3% |
| rIFNτ-1b | 95.3% |
| GM-CSF | 94.7% |
| G-CSF | 89.5% |
| rTNF | 80.6% |
| Intermediate Sensitivity | |
| nHuIFNπ | 79.8% |
| rIFNβ-1b | 73.6% |
| Resistant | |
| Doxorubicin | 8.6% |
| Ara-C | 8.0% |
| Prednisone | 7.2% |
| BCNU | 5.6% |
| rIFNα-2a | 5.4% |
| Cyclophosphamide | 1.6% |
| Retinoic acid | 0.0% |
| Cisplatin | 0.0% |
| 5-FU | 0.0% |
| Amethopterin | 0.0% |
| VCR | 0.0% |
| Somatostatin | 0.0% |
| nHuIFNα | 0.0% |
| rIL-2 | 0.0% |

The positive (Abrin) control sample demonstrated 91.0% cell kill as compared to the negative control sample.

Experiment 27: Patient (27) suffered from pleomorphic adenocarcinoma. A tumor sample was tested by the preferred embodiment of the pharmacosensitivity assay as set out above and the following results were obtained:

| | |
|---|---|
| High Sensitivity | |
| nHuIFNα | 81.6% |
| Intermediate Sensitivity | |
| nHuIFNβ | 78.4% |
| nHuIFNπ | 77.9% |
| rTNF | 77.4% |
| G-CSF | 76.5% |
| GM-CSF | 72.4% |
| Doxorubicin | 53.9% |
| Low Sensitivity | |
| BCNU | 25.0% |
| Resistant | |
| Amethopterin | 11.0% |
| Prednisone | 6.3% |
| Ifosfamide | 5.0% |
| Mito-C | 3.1% |
| VCR | 3.0% |
| Cyclophosphamide | 2.5% |
| Dactinomycin | 2.3% |
| Fludarabine phosphate | 2.0% |
| rIFNβ-1b | 3.4% |
| VBL | 1.6% |
| Bleomycin | 1.5% |
| DTIC | 1.3% |
| Ifosfamide/Mesna | 1.4% |
| rIFNα-2a | 1.1% |
| rIFNτ-1b | 0.5% |
| Ara-C | 0.4% |
| Retinoic acid | 0.0% |
| Hydrea | 0.0% |
| Cisplatin | 0.0% |
| 5-FU | 0.0% |
| Somatostatin | 0.0% |
| rIL-2 | 0.0% |

The positive (Abrin) control sample demonstrated 71.7% cell kill as compared to the negative control sample.

Experiment 29: Patient (28) suffered from melanoma. A tumor sample was tested by the preferred embodiment of the pharmacosensitivity assay as set out above and the following results were obtained:

| | |
|---|---|
| Intermediate Sensitivity | |
| VBL | 75.6% |
| Doxorubicin | 72.1% |
| Ara-C | 74.5% |
| Bleomycin | 69.4% |
| Cyclophosphamide | 67.3% |
| DTIC | 55.9% |
| Mito-C | 48.9% |
| Etoposide | 47.5% |
| Taxol | 43.2% |
| Tamoxifen | 35.6% |

-continued

Low Sensitivity

| | |
|---|---|
| G-CSF | 34.0% |
| VCR | 32.1% |
| Hydrea | 31.5% |
| Mechlorethamine hydrochloride | 26.7% |
| Ifosfamide/Mesna | 26.0% |
| nHuIFNβ | 24.8% |
| GM-CSF | 24.5% |
| BCNU | 23.0% |
| rIFNα-2a | 22.3% |
| Fludarabine phosphate | 21.8% |
| Cisplatin | 20.9% |
| Ifosfamide | 20.7% |

Resistant

| | |
|---|---|
| nHuIFNπ | 19.9% |
| rIFNβ-1b | 19.9% |
| rIFNτ-1b | 16.7% |
| Somatostatin | 15.7% |
| rIL-2 | 15.0% |
| rTNF | 12.8% |
| nHuIFNα | 12.8% |
| Retinoic acid | 0.5% |
| 5-FU | 0.0% |

The positive (Abrin) control sample demonstrated 94.5% cell kill as compared to the negative control sample.

Experiment 29: 78 patients having liver metastases were treated by use of the procedure. The primary tumors were: breast 14; renal cell 8; colorectal 14; lung adenocarcinoma 12; melanoma 12; ovarian 8; primary liver 5; and salivary gland 5. All patients were previously unsuccessfully treated with conventional therapy. Tumor tissue was obtained by biopsy of the liver, and thus the metastases provided the basis for the pharmacosensitivity assay. A catheter was introduced percutaneously to the common hepatic artery or implanted during surgery. A combination of systemic and locoregional chemotherapy was administered 8 times for 3 hours every 4 weeks, with drugs and dosages chosen according to the assay. 43 drugs were tested with the assay, 5 of these being biological response modifiers. All 78 patients' tumors demonstrated sensitivity to doxorubicin, mito-C, cisplatin and interferon alpha (IFNα). Patients with the following tumors also demonstrated sensitivity to the following drugs: carboplatin for ovarian and lung cancer; floxuridine for colon cancer; methotrexate for breast and salivary gland cancer; dacarbazine for melanoma; etoposide for renal cell and primary liver cancer; and bleomycin for salivary gland cancer. It is hypothesized that the correlation between the pharmacosensitivity of the metastases and the type of the primary tumor involved is a reflection of the particular weaknesses of the primary tumor cell lines.

After 4 courses of treatment, 23 patients achieved complete remission for 8 or more months; partial remission was achieved in 35 patients for up to 24 months; no change was achieved in 14 patients for 8 months; and 16 patients demonstrated disease progression. Side-effects of nausea, vomiting, leukopenia, anemia and thrombocytopenia were experienced, but all were transitory and of short duration. The experiment showed that the procedure offers an effective choice of drugs for overall treatment, i.e., simultaneous treatment of both primary tumors and (liver) metastases, with minimal side-effects.

Experiment 30: In 17 patients (average age 57 years, varying from 32–71 years; 6 females, 11 males) suffering from colon carcinoma with liver metastases, an intra-arterial, intra-hepatic catheter was implanted. Tumor tissue was obtained by liver biopsy during this procedure, and thus the liver tumors provided the basis for the pharmacosensitivity assay. During the assay, the tumor was tested with 26 drugs (including 5 biological response modifiers). Drug sensitivity to the same drugs varied considerably amongst the patients. The four most active drugs for each patient, plus interferon alpha (IFNα) were administered to each patient, and each drug was administered at the highest recommended dosage. Systemic chemotherapy was applied, and one-day locoregional infusion was administered every 4 weeks. Complete remission was obtained in 5 patients for at least 18 months, and three patients are still in complete remission after 3 years. Partial remission was obtained in 10 patients, varying in duration from 8 and 24 months. No change was obtained for 1 patient for 8 months. One patient showed disease progression. Minimal side-effects (nausea, vomiting, thrombocytopenia) were observed. The experiment showed that the procedure offers an effective choice of drugs for liver metastases of colon carcinoma when given in locoregional infusion, with minimal side-effects.

Experiment 31: 14 patients suffering from pancreatic cancer with extensive liver metastases were treated by use of the procedure (median age 56, age from 32–78, 2 females, 12 males). Liver tumor cells were tested with 30 drugs (including 6 biological response modifiers and 3 hormones). Doxorubicin, methotrexate, floxuridine, streptozotocin, BCNU, mito-C, cis-platinum, carboplatin, and interferons alpha and gamma (IFNα and IFNτ) were found to have activity in the pharmacosensitivity assay. A percutaneously introduced intra-arterial, intra-hepatic catheter was administered directly to the pancreas and the liver (with approximately 33% delivery to the pancreas and 67% to the liver). The four most active drugs for each patient and IFNα and IFNτ were used for the respective patient. Over 3 hours of locoregional infusion were administered every 4 weeks for 6 weeks along with systemic administration.

2 patients achieved complete remission for 18 or more months (with both patients being alive after 3 years). 8 patients achieved partial remission; 6 of these had radical surgery, 4 with complete resection. Partial remission was achieved for between 8 and 24 months. 1 patient achieved no change for 6 months. Minimal side effects were observed. The experiment showed that the procedure offers an effective choice of drugs for pancreatic cancer and liver metastases with minimal side-effects.

Experiment 32: 21 patients suffering from colon cancer with liver metastases were treated by the procedure (average age 61, from 35–75 years of age, 8 females, 13 males). All patients failed to respond to previous extensive therapy. The pharmacosensitivity assay was performed on liver tumor cells with 26 drugs (5 of which were biological response modifiers). Doxorubicin, methotrexate, fluoruracil, floxuridine, BCNU, ara-C, streptozotocin and interferon alpha (IFNα) were found to have good activity against the colon cancer cells. The 5 most active drugs for each patient and interferon alpha were administered once every 4 weeks for 6 weeks by intra-arterial, intra-hepatic catheter, and also by general systemic administration.

7 patients achieved complete remission for 24 or more months, with 4 patients still in complete remission after 4 years. Partial remission was achieved in 7 patients for 7 to 35 months; of these, 4 had complete liver resection and 1 had partial liver resection after the chemotherapy was completed. 6 patients demonstrated no change for 8 months. 1 patient showed disease progression. Minimal side-effects (leukopenia and thrombocytopenia) were observed and were reversible. The experiment showed that the procedure offers an effective choice of drugs for colon cancer with liver metastases with minimal side-effects.

Experiment 33: 86 cancer patients with liver metastases, all of which were previously treated unsuccessfully with conventional therapy, had primary tumors were of the digestive tract (39 patients); genito-urinary tract (10 patients); breast (18 patients); respiratory system (11 patients); and melanoma (8 patients). A catheter was introduced percutaneously to the hepatic artery or implanted during surgery. 30.0 mg of tolazoline hydrochloride was injected intra-arterially to dilate the hepatic artery immediately after placement of the catheter and before chemotherapy. Liver tumor cells demonstrated sensitivity to doxorubicin, mito-C, cisplatin and interferon alpha in the pharmacosensitivity assay and were used for all 86 patients. Two additional drugs (as per patient tumor response) were added to this regimen for each patient. Each patient was treated systemically and intra-arterially for over 3 hours per day, one day every 4 weeks, for 6 courses. Complete remission was achieved in 24 patients with a duration of 8 or more months. 35 patients achieved partial remission for 8–24 months. 24 patients demonstrated NC for 8 months. 3 patients were nonresponsive. Minimal transitory side effects were observed. No local toxicity to the vessels, liver or gallbladder occurred. The experiment showed that the procedure allowed a choice of an effective chemotherapeutic regimen for cancer with liver metastases.

It is understood that the invention is not limited to the particular apparatus and arrangement of steps herein described, but embraces any modified forms that fall within the scope of the following claims.

BIBLIOGRAPHY

Lacombe et al., "Detection of cytarabine resistance in patients with acute myelogenous leukemia using flow cytometry," *Blood*, v84: 716–723 (1994).

Smit et al., "In vitro response of human small-cell lung-cancer cell lines to chemotherapeutic drugs: no correlation with clinical data," *International Journal of Cancer*, v51: 72–78 (1992).

Salmon et al. "Primary bioassay of human tumor stem cells," *Science*, v197: 461–463 (1977).

Mossmann, "Rapid calorimetric assay for cellular growth and survival: application to proliferation and cytotoxic assays," *Journal of Immunological Methods*, v65, 55–63 (1983).

Hwang et al., "Prediction of chemotherapy response in human leukemia using in vitro chemosensitivity test," *Leukemia Research*, v17: 685–688 (1993).

Schadendorf et al., "Chemosensitivity testing of human malignant melanoma," *Cancer*, v73, 103–108 (1993).

DeVita, Cancer Principles & Practice of Oncology, J. B. Lippincott Co., 3d ed., 1989.

Arvelo et al., "Response of a multi-drug resistant human small-cell lung cancer xenograft to chemotherapy," *Journal of Cancer Research and Clinical Oncology*, v120: 17–23 (1993).

Van de Loosdrecht et al., "Apoptosis in tumor necrosis factor-alpha-dependent, monocyte-mediated leukemic cell death: a functional, morphologic, and flow-cytometric analysis," *Experimental Hematology*, v21: 1628–1639 (1993).

Darzynkiewicz et al., "Features of apoptotic cells measured by flow cytometry," *Cytometry*, v13: 795–808 (1992).

Christ et al., "Apoptosis induced by oxysterols in murine lymphoma cells and in normal thymocytes," *Immunology*, v78, 455–460 (1993).

Elprana et al., "Chemosensitivity testing of xenografted squamous cell carcinomas of the head and neck region," *Anticancer Research*, v12, 229–2240 (1992).

Camparia et al., "Stroma-supported immunocytometric assay (SIA): a novel method for testing the sensitivity of acute lymphoblastic leukemia cells to cytotoxic drugs," *Leukemia*, v7: 482–488 (1993).

Dao et al., "Natural human interferon-augments apoptosis in activated T-cell line," *Cellular Immunology*, v155: 304–311 (1994).

Thoth et al., "Type I interferon resistance in a colorectal cancer cell line is associated with a more aggressive phenotype in vivo," *British Journal of Cancer*, v65: 365–368 (1992).

Fluckiger et al., "Interleukin 10 induces apoptotic cell death of B-chronic lymphocytic leukemia cells," *Journal of Experimental Medicine*, v179: 91–99 (1994).

Nicoletti et al., "A rapid and simple method for measuring thymocyte apoptosis by propidium iodide staining and flow cytometry," *Journal of Immunological Methods*, v139: 271–279 (1991).

Bryson, "A flow cytometric study of cell death: failure of some models to correlate with morphological assessment," *Immunology and Cell Biology*, v72, 35–41 (1994).

Huschtscha et al., "Identification of apoptotic and necrotic human leukemic cells by flow cytometry," *Experimental Cell Research*, v212: 161–165 (1994).

Sun et al., "A flow-cytometric method for the separation and quantitation of normal and apoptotic thymocytes," *Analytical Biochemistry*, v204, 351–356 (1992).

What is claimed is:

1. A method for treating non-leukemic cancers in humans comprising:

(a) preparing a cancer cell suspension from a cancer specimen obtained from a human non-leukemic cancer patient;

(b) preparing a control sample from the cancer cell suspension;

(c) preparing several drug samples from several putative cancer cell growth-inhibiting drugs and the cancer cell suspension, each drug sample containing a mixture of the cancer cell suspension and at least one drug; and then (d) incubating the control sample and drug samples; then (e) staining the control samples and drug sample with a DNA intercalating dye; then (f) determining the cancer cell viability in the control sample and the drug samples by use of a flow cytometer and determining the white cell content of the cancer cell suspension and adjusting the determined cancer cell viability of each drug sample and the control sample to compensate for the white cell content of each, whereby an adjusted cancer cell viability of each drug sample and the control sample is obtained; then (g) comparing the adjusted cancer cell viability of each drug sample with the adjusted cancer cell viability of the control sample; and then (h) preparing a drug treatment regimen for the human non-leukemic cancer patient containing selected drugs chosen from the several cancer cell growth-inhibiting drugs, the selected drugs corresponding to the drugs in the drug samples having the lowest adjusted cancer cell viability in comparison to the control sample; and then (i) administering the drug treatment regimen to the human non-leukemic cancer patient in an amount which is effective to inhibit the growth of the cancer.

2. The method of claim 1 wherein step c further comprises calculating the viable cancer cell concentration within the cancer cell suspension, and wherein each drug contained within each drug sample is added in a predetermined aliquot amount proportional to the viable cancer cell concentration.

3. The method of claim 2 wherein each drug sample includes at least one of the following drugs at the following aliquot amounts, and wherein each drug contained within each drug sample is diluted by a pharmaceutical diluent proportionally to a viable cancer cell concentration of about $1 \times 10^6$ cells/ml:

amethopterin, 0.25 mg/3.0 ml;
ara-C, 0.60 mg/ml;
BCNU, 0.003 mg/3.0 ml;
bleomycin, 0.05 u/ml;
cis-platin, 0.03 mg/3.0 ml;
cladribine, 0.01 mg/ml;
cyclophosphamide, 0.020 mg/3.0 ml;
dactinomycin, 0.015 mg/ml;
doxorubicin, 0.02 mg/3.0 ml;
DTIC, 0.1 mg/3.0 ml;
etoposide, 0.20 mg/3.0 ml;
fludarabine phosphate, 0.25 mg/3.0 ml;
5-FU, 0.50 mg/3.0 ml;
floxuridine, 0.2 mg/3.0 ml;
hydrea, 0.50 mg/ml;
idamycin, 0.001 mg/3.0 ml;
ifosfamide, 1.5 mg/ml;
levamisole, 0.05 mg/3.0 ml;
mechlorethamine hydrochloride, 0.01 mg/3.0 ml;
medroxyprogesterone, 1.50 mg/3.0 ml;
megestrol acetate, 0.008 mg/3.0 ml;
melphalan, 0.0002 mg/3.0 ml;
mesna, 3.0 mg/3.0 ml;
mito-C, 0.005 mg/ml;
octreotide acetate, 5.0 ug/3.0 ml;
paraplatin, 0.05 mg/ml;
prednisone, 0.6 mg/ml;
retinoic acid, 0.04 mg/3.0 ml;
somatostatin, 5.0 ug/3.0 ml;
streptozocin, 1.0 mg/3.0 ml;
tamoxifen, 0.003 mg/3.0 ml;
taxol, 0.06 mg/3.0 ml;
thio-TEPA, 0.025 mg/ml;
VBL, 0.03 mg/ml; and
VCR, 0.01 mg/ml.

4. The method of claim 2 wherein each drug sample includes at least one of the following drugs at the following aliquot amounts, and wherein each drug contained within each drug sample is diluted by a pharmaceutical diluent proportionally to a viable cancer cell concentration of about $1 \times 10^6$ cells/ml:

rIFNα-2a, 30,000 u/ml;
rIL-2, 10 u/ml;
rIFNα-2b, 1,000 neutralizing units/ml;
nHuIFNα, $1 \times 10^3$ u/ml;
nHuIFNβ, $1 \times 10^3$ u/ml;
nHuIFNπ, $5 \times 10^2$ u/ml;
rIFNβ-1b, $1 \times 10^3$ u/ml;
rIFNτ-1b, 0.01 μg/ml;
TNF, $1.2 \times 10^2$ u/ml;
GM-CSF, 62.5 u/ml; and
G-CSF, 200 u/ml.

5. The method of claim 1 wherein the control sample is a negative control sample, and wherein step (b) further comprises the steps of:

(i) preparing a positive control sample containing the cancer cell suspension and a toxin; then (ii) incubating the positive control sample; then (iii) determining the cancer cell viability in the positive control sample and determining the white cell content of the positive control sample and adjusting the determined cancer cell viability of the positive control sample to compensate for the white cell content thereof; and then (iv) comparing the adjusted cancer cell viability of the positive control sample with the adjusted cancer cell viability of the negative control sample.

6. A method for treating non-leukemic cancers in humans comprising:

(a) preparing a cancer cell suspension from a human non-leukemic cancer patient's cancer specimen; then (b) calculating the viable cancer cell count within the cancer cell suspension; then (c) adjusting the volume of the cancer cell suspension to obtain a base cell concentration by diluting the cancer cell suspension with patient medium in proportion with the viable cancer cell count; then (d) preparing a negative control sample from the cancer cell suspension; and (e) preparing drug samples, each drug sample containing a mixture of cancer cell suspension, patient medium, and a drug selected from several putative cancer cell growth-inhibiting drugs, wherein each drug sample contains a different drug which is added to the drug sample in an aliquot amount proportional to the base cell concentration; then (f) incubating the drug samples and negative control sample; then (g) staining the drug samples and negative control sample with a DNA intercalating dye; then (h) determining the cancer cell viability in the drug samples and negative control sample by use of a flow cytometer and determining the white cell content of the cancer cell suspension and adjusting the determined cancer cell viability of each drug sample and the control sample to compensate for the white cell content of each, whereby an adjusted cancer cell viability of each drug sample and the control sample is obtained; and then (i) comparing the adjusted cancer cell viability in the drug samples and negative control sample to determine the pharmacosensitivity of the cancer cells; and then (j) preparing a drug treatment regimen containing one or more selected drugs chosen from the several cancer cell growth-inhibiting drugs, the selected drugs corresponding to the drug samples having the lowest adjusted cancer cell viability; and then (k) administering the drug treatment regimen to the human non-leukemic cancer patient in an amount which is effective to inhibit the growth of the cancer.

7. The method of claim 6 wherein step (d) further comprises (i) preparing a positive control sample from the cancer cell suspension; then (ii) incubating the positive control sample; then (iii) staining the positive control sample with a DNA intercalating dye; and then (iv.) determining the cancer cell viability in the positive control sample by use of a flow cytometer and determining the white cell content of the positive control sample and adjusting the determined cancer cell viability of the positive control sample to compensate for the white cell content thereof.

8. The method of claim 6 wherein in step (a) the cancer specimen is taken from a non-leukemic metastatic tumor in a human cancer patient suffering from a non-leukemic primary tumor and a non-leukemic metastatic tumor.

9. The method of claim 8 wherein the drug treatment regimen is administered locoregionally.

10. The method of claim 1 wherein in step (a) the cancer specimen is taken from a non-leukemic metastatic tumor in a human cancer patient suffering from a non-leukemic primary tumor and a non-leukemic metasiatic tumor.

11. The method of claim 1 wherein the metastatic tumor is a metastatic tumor of the liver, and further wherein the drug treatment regimen is administered locoregionally via the hepatic artery.

12. The method of claim 1 wherein in step (i) the drug treatment regimen is administered locoregionally.

13. The method of claim 1 wherein in step (i) at least one biological response modifier is administered.

14. The method of claim 1 wherein in step (i) an alpha interferon and a hormone are administered.

* * * * *